(12) United States Patent
Naglik et al.

(10) Patent No.: US 9,969,796 B2
(45) Date of Patent: May 15, 2018

(54) PEPTIDES AND BINDING PARTNERS THEREFOR

(71) Applicants: KING'S COLLEGE LONDON, London (GB); LEIBNIZ INSTITUT FUR NATURSTOFF-FORSCHUNG UND INFEKTIONSBIOLOGIE E.V., Jena (DE)

(72) Inventors: Julian Naglik, London (GB); David Moyes, London (GB); Shirley Tang, London (GB); Bernhard Hube, Jena (DE); Duncan Wilson, Jena (DE); Sarah Hofs, Jena (DE); Jonathan Richardson, London (GB)

(73) Assignees: KING'S COLLEGE LONDON, London (GB); LEIBNIZ INSTITUT FUR NATURSTOFF-FORSCHUNG UND INFEKTIONSBIOLOGIE E.V., Jena (DE)

( * ) Notice: Subject to any disclaimer, the term of this patent is extended or adjusted under 35 U.S.C. 154(b) by 48 days.

(21) Appl. No.: 14/783,237

(22) PCT Filed: Apr. 10, 2014

(86) PCT No.: PCT/GB2014/051118
§ 371 (c)(1),
(2) Date: Oct. 8, 2015

(87) PCT Pub. No.: WO2014/167335
PCT Pub. Date: Oct. 16, 2014

(65) Prior Publication Data
US 2016/0046699 A1 Feb. 18, 2016

(30) Foreign Application Priority Data

Apr. 11, 2013 (GB) .................................. 1306588.3

(51) Int. Cl.
| | | |
|---|---|---|
| *A61K 39/00* | (2006.01) | |
| *C07K 16/14* | (2006.01) | |
| *C07K 14/40* | (2006.01) | |
| *A61K 39/39* | (2006.01) | |
| *A61K 39/395* | (2006.01) | |
| *G01N 33/68* | (2006.01) | |

(52) U.S. Cl.
CPC .......... *C07K 16/14* (2013.01); *A61K 39/0002* (2013.01); *A61K 39/39* (2013.01); *A61K 39/39575* (2013.01); *C07K 14/40* (2013.01); *G01N 33/6845* (2013.01); *A61K 2039/52* (2013.01); *G01N 2500/04* (2013.01); *G01N 2500/20* (2013.01)

(58) Field of Classification Search
None
See application file for complete search history.

(56) References Cited

U.S. PATENT DOCUMENTS 6,747,137 B1 * 6/2004 Weinstock ........... C12Q 1/6895
435/6.13
2012/0237534 A1 9/2012 Fu et al.

FOREIGN PATENT DOCUMENTS

| WO | 01/38550 A2 | 5/2001 |
| WO | 2006/036817 A2 | 4/2006 |
| WO | 2014/167335 A1 | 10/2014 |

OTHER PUBLICATIONS

Bader et al., "Processing of predicted substrates of fungal Kex2 proteinases from Candida albicans, C. glabrata, *Saccharomyces cerevisiae* and Pichia pastoris", BMC Microbiology, 2008, 16 pgs., vol. 8.
Birse et al., "Cloning and Characterization of ECE1, a Gene Expressed in Association with Cell Elongation of the Dimorphic Pathogen Candida albicans", Infection and Immunity, 1993, pp. 3648-3655, vol. 61, No. 9.
Dalle et al., "Cellular interactions of Candida albicans with human oral epithelial cells and enterocytes", Cellular Microbiology, 2010, pp. 248-271, vol. 12, No. 2.
GenBank Accession No. DQ465877, dated Jun. 17, 2009; 2 pgs.
Great Britian Search Report from related Application No. GB1306588.3, dated Oct. 9, 2013; 5 pgs.
International Search Report and Written Opinion from related International Application No. PCT/GB2014/051118, dated Aug. 11, 2014; 13 pgs.
Lain et al., "Use of Recombinant Antigens for the Diagnosis of Invasive Candidiasis", Clinical and Developmental Immunology, 2008, pp. 3284-3287, vol. 35, No. 12.
Moyes et al., "A Biphasic Innate Immune MAPK Response Discriminates between the Yeast and Hyphal Forms of Candida albicans in Epithelial Cells", Cell Host & Microbe, 2010, pp. 225-235, vol. 8.
Moyes et al., "Candida albicans Yeast and Hyphae are Discriminated by MAPK Signaling in Vaginal Epithelial Cells", PLoS ONE, 2011, e26580, vol. 6, No. 11, 9 pgs.
Moyes et al., "Activation of MAPK/c-Fos induced responses in oral epithelial cells is specific to Candida albicans and Candida dubliniensis hyphae", Med Microbiol Immunol., 2012, pp. 93-101, vol. 201, No. 1.
Moyes et al., "Analysis of Host-Cell Responses by Immunoblotting, ELISA, and Real-Time PCR", Methods in Molecular Biology, 2012, pp. 345-360, vol. 845.

(Continued)

*Primary Examiner* — Jennifer E Graser

(57) ABSTRACT

The invention provides a peptide obtainable from *C. albicans* as well as variants and fragments thereof, and labelled forms of these. The peptide is immunogenic and specific binding partners for the peptide and labelled forms of these specific binding partners form a further aspect of the invention. The peptide is a fragment of the ECE1 protein and has been found to be both immunogenic and act as a pore-forming toxin. A range of therapeutic and diagnostic applications for the peptide and the specific binding partners for it form further aspects of the invention. In addition, the peptide may be used in screens for identifying compounds having useful anti-fungal activity.

7 Claims, 13 Drawing Sheets

(56) References Cited

OTHER PUBLICATIONS

Figure 1A:
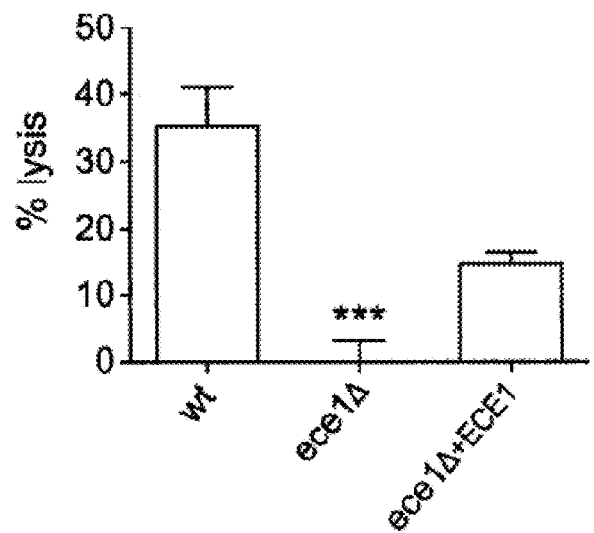

Murad et al., "Clp10, an efficient and convenient integrating vector for Candida albicans", Yeast, 2000; pp. 325-327, vol. 16.

Murciano et al., "Candida albicans Cell Wall Glycosylation May Be Indirectly Required for Activation of Epithelial Cell Proinflammatory Responses", Infection and Immunity, 2011, pp. 4902-4911, vol. 79, No. 12.

Murciano et al., "Evaluation of the Role of Candida albicans Agglutinin-Like Sequence (Als) Proteins in Human Oral Epithelial Cell Interactions", PloS ONE, 2012, e33362, vol. 7, No. 3, 9 pgs.

Ramsook et al., "Yeast Cell Adhesion Molecules Have Functional Amyloid-Forming Sequences", Eukaryotic Cell, 2010, pp. 393-404, vol. 9, No. 3.

Wachtler et al., "Candida albicans Adhesion to and Invasion and Damage of Vaginal Epithelial Cells: Stage-Specific Inhibition by Clotrimazole and Bifonazole", Antimicrobial Agents and Chemotherapy, 2011, pp. 4436-4439, vol. 55, No. 9.

Wachtler et al., "From Attachment to Damage: Defined Genes of Candida albicans Mediate Adhesion, Invasion and Damage during Interaction with Oral Epithelial Cells", PLoS ONE, 2011, e17046, vol. 6, No. 2, 14 pgs.

\* cited by examiner

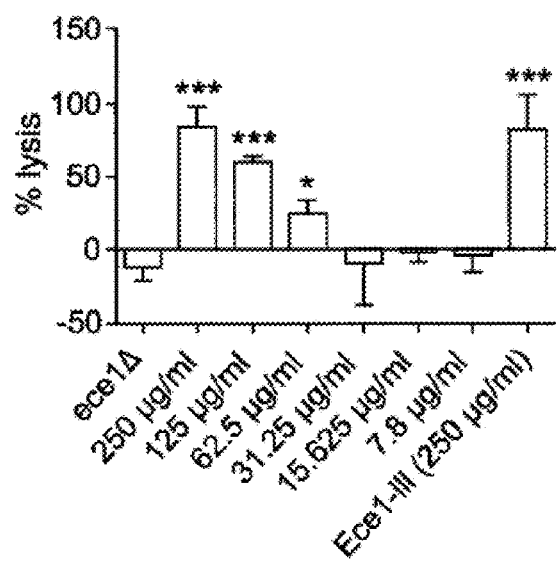
FIGURE 3A
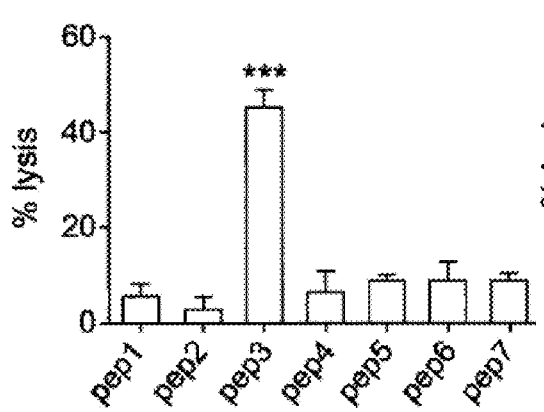   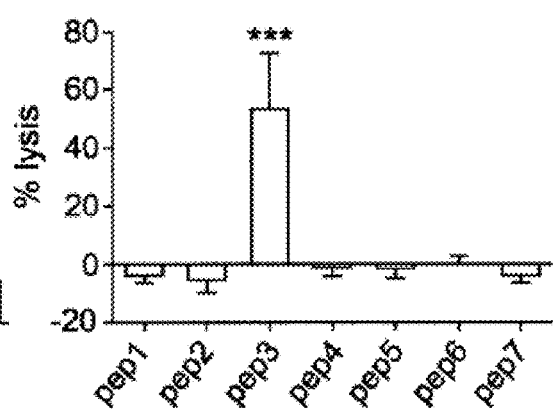
FIGURE 3B                    FIGURE 3C

Ece1-III:  SIIGIIMGILGNIPQVIQIIMSIVKAFKGNKR   (SEQ ID NO 1)

| WTSA 1: | SIIGIIMGIL | (SEQ ID NO 8) |
| WTSA 2: | SIIGIIMGILGNIP | (SEQ ID NO 9) |
| WTSA 3: | SIIGIIMGILGNIPQVIQIIMSIV | (SEQ ID NO 10) |
| WTSA 4: | GNIPQVIQIIMSIV | (SEQ ID NO 11) |
| WTSA 5: | QVIQIIMSIV | (SEQ ID NO 3) |
| WTSA 6: | KAFKGNKR | (SEQ ID NO 12) |

SEQUENCE LISTING

```
<160> NUMBER OF SEQ ID NOS: 18

<210> SEQ ID NO 1
<211> LENGTH: 32
<212> TYPE: PRT
<213> ORGANISM: Candida albicans

<400> SEQUENCE: 1

Ser Ile Ile Gly Ile Ile Met Gly Ile Leu Gly Asn Ile Pro Gln Val
1               5                   10                  15

Ile Gln Ile Ile Met Ser Ile Val Lys Ala Phe Lys Gly Asn Lys Arg
            20                  25                  30

<210> SEQ ID NO 2
<211> LENGTH: 9
<212> TYPE: PRT
<213> ORGANISM: Candida albicans

<400> SEQUENCE: 2

Ile Ile Gly Ile Ile Met Gly Ile Leu
1               5

<210> SEQ ID NO 3
<211> LENGTH: 10
<212> TYPE: PRT
<213> ORGANISM: Candida albicans

<400> SEQUENCE: 3

Gln Val Ile Gln Ile Ile Met Ser Ile Val
1               5                   10

<210> SEQ ID NO 4
<211> LENGTH: 122
<212> TYPE: DNA
<213> ORGANISM: Artificial Sequence
<220> FEATURE:
<223> OTHER INFORMATION: SYNTHESIZED

<400> SEQUENCE: 4
atcaaataac ccacctattt caaaattgtt ttatttttgt ttatctctac aacaaacaac      60
tttcctttat tttactacca actattttcc attcgttaaa gaagcttcgt acgctgcagg     120
tc                                                                    122

<210> SEQ ID NO 5
<211> LENGTH: 127
<212> TYPE: DNA
```

```
<213> ORGANISM: Artificial Sequence
<220> FEATURE:
<223> OTHER INFORMATION: SYNTHESIZED

<400> SEQUENCE: 5
cacaaaaaac aacaattaaa aaaatcagtt acagcaaaag tgtcacaaga cttatggaat      60
aaaagattaa gcttgtggaa aacaaatttt tatctgctga gcattctgat atcatcgatg     120
aattcga                                                               127

<210> SEQ ID NO 6
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 6

Gly Cys Ala Cys Gly Cys Gly Thr Cys Thr Ala Ala Ala Gly Thr Gly
1               5                   10                  15

Gly Ala Gly Thr Ala Ala Cys Ala Ala Cys
            20                  25

<210> SEQ ID NO 7
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 7
ggtcgacccc agacgttggt tgc                                              23

<210> SEQ ID NO 8
<211> LENGTH: 10
<212> TYPE: PRT
<213> ORGANISM: Candida albicans

<400> SEQUENCE: 8

Ser Ile Ile Gly Ile Ile Met Gly Ile Leu
1               5                   10

<210> SEQ ID NO 9
<211> LENGTH: 14
<212> TYPE: PRT
<213> ORGANISM: Candida albicans

<400> SEQUENCE: 9

Ser Ile Ile Gly Ile Ile Met Gly Ile Leu Gly Asn Ile Pro
1               5                   10

<210> SEQ ID NO 10
<211> LENGTH: 24
<212> TYPE: PRT
<213> ORGANISM: Candida albicans

<400> SEQUENCE: 10

Ser Ile Ile Gly Ile Ile Met Gly Ile Leu Gly Asn Ile Pro Gln Val
1               5                   10                  15

Ile Gln Ile Ile Met Ser Ile Val
            20

<210> SEQ ID NO 11
<211> LENGTH: 14
```

```
<212> TYPE: PRT
<213> ORGANISM: Candida albicans

<400> SEQUENCE: 11

Gly Asn Ile Pro Gln Val Ile Gln Ile Ile Met Ser Ile Val
1               5                   10

<210> SEQ ID NO 12
<211> LENGTH: 8
<212> TYPE: PRT
<213> ORGANISM: Candida albicans

<400> SEQUENCE: 12

Lys Ala Phe Lys Gly Asn Lys Arg
1               5

<210> SEQ ID NO 13
<211> LENGTH: 271
<212> TYPE: PRT
<213> ORGANISM: Candida albicans

<400> SEQUENCE: 13

Met Lys Phe Ser Lys Ile Ala Cys Ala Thr Val Phe Ala Leu Ser Ser
1               5                   10                  15

Gln Ala Ala Ile Ile His His Ala Pro Glu Phe Asn Met Lys Arg Asp
                20                  25                  30

Val Ala Pro Ala Ala Pro Ala Ala Pro Ala Asp Gln Ala Pro Thr Val
            35                  40                  45

Pro Ala Pro Gln Glu Phe Asn Thr Ala Ile Thr Lys Arg Ser Ile Ile
50                  55                  60

Gly Ile Ile Met Gly Ile Leu Gly Asn Ile Pro Gln Val Ile Gln Ile
65                  70                  75                  80

Ile Met Ser Ile Val Lys Ala Phe Lys Gly Asn Lys Arg Glu Asp Ile
                85                  90                  95

Asp Ser Val Val Ala Gly Ile Ile Ala Asp Met Pro Phe Val Val Arg
            100                 105                 110

Ala Val Asp Thr Ala Met Thr Ser Val Ala Ser Thr Lys Arg Asp Gly
            115                 120                 125

Ala Asn Asp Asp Val Ala Asn Ala Val Arg Leu Pro Glu Ile Val
130                 135                 140

Ala Arg Val Ala Thr Gly Val Gln Gln Ser Ile Glu Asn Ala Lys Arg
145                 150                 155                 160

Asp Gly Val Pro Asp Val Gly Leu Asn Leu Val Ala Asn Ala Pro Arg
                165                 170                 175

Leu Ile Ser Asn Val Phe Asp Gly Val Ser Glu Thr Val Gln Gln Ala
            180                 185                 190

Lys Arg Asp Gly Leu Glu Asp Phe Leu Asp Glu Leu Leu Gln Arg Leu
            195                 200                 205

Pro Gln Leu Ile Thr Arg Ser Ala Glu Ser Ala Leu Lys Asp Ser Gln
            210                 215                 220

Pro Val Lys Arg Asp Ala Gly Ser Val Ala Leu Ser Asn Leu Ile Lys
225                 230                 235                 240

Lys Ser Ile Glu Thr Val Gly Ile Glu Asn Ala Ala Gln Ile Val Ser
                245                 250                 255

Glu Arg Asp Ile Ser Ser Leu Ile Glu Glu Tyr Phe Gly Lys Ala
            260                 265                 270
```

-continued

```
<210> SEQ ID NO 14
<211> LENGTH: 268
<212> TYPE: PRT
<213> ORGANISM: Candida dubliniensis

<400> SEQUENCE: 14
```

Met Lys Phe Ser Lys Ile Ala Cys Ala Ala Phe Val Leu Ser Ser
1               5                   10                  15

Gln Ala Ala Ile Ile His His Ala Pro Glu Phe Asn Met Lys Arg Asp
            20                  25                  30

Ile Ala Thr Ala Asp Pro Val Ala Glu Pro Asp Val Ser Val Ala
        35                  40                  45

Ala Asn Val Asp Thr Ser Ile Ala Lys Arg Ser Ile Ile Gly Ile Leu
    50                  55                  60

Thr Ala Ile Leu Asn Asn Val Pro Gln Ile Ile Asn Val Ile Thr Thr
65                  70                  75                  80

Ile Ile Lys Ser Ile Thr Gly Asn Lys Arg Glu Asp Ile Asp Ser Val
                85                  90                  95

Val Ser Gly Val Ile Ala Asp Met Pro Phe Val Val Arg Ala Val Asp
            100                 105                 110

Thr Ala Leu Thr Ser Val Ala Ser Thr Lys Arg Asp Gly Thr Asn Asp
        115                 120                 125

Asp Val Thr Asn Ala Ile Val Arg Leu Pro Glu Ile Val Ala Pro Val
    130                 135                 140

Ala Thr Gly Val Gln Gln Thr Val Glu Asn Ala Lys Arg Asp Gly Val
145                 150                 155                 160

Glu Asp Ile Gly Leu Asn Ile Val Ala Asn Ser Pro Arg Leu Val Ser
                165                 170                 175

Asp Val Ile Gly Gly Val Ser Glu Thr Val Lys Gln Ala Lys Arg Asp
            180                 185                 190

Asn Ala Glu Asp Ile Leu Thr Lys Val Leu Gln Glu Leu Pro Asp Ile
        195                 200                 205

Ile Ser Lys Val Ser Asn Ser Thr Leu Lys Asn Ser Pro Pro Phe Lys
    210                 215                 220

Arg Asp Ala Asn Thr Val Thr Leu Ser Lys Leu Ile Lys Lys Ser Ile
225                 230                 235                 240

Glu Thr Ile Gly Val Glu Asn Ala Ala Lys Met Val Ser Lys Arg Asp
                245                 250                 255

Ile Ser Ser Leu Ile Ala Glu Tyr Phe Glu Glu Ala
            260                 265

```
<210> SEQ ID NO 15
<211> LENGTH: 282
<212> TYPE: PRT
<213> ORGANISM: Candida tropicalis

<400> SEQUENCE: 15
```

Met Lys Phe Ser Lys Val Ala Ser Phe Ala Phe Leu Ala Leu Ser Ser
1               5                   10                  15

Gln Ala Ala Leu Ile Gln His Asp Val Ile Glu Asn Ile Lys Arg
            20                  25                  30

Asp Ala Val Leu Ala Gly Ser Ala Glu Asn Ile Ala Ser Ser Ala
    35                  40                  45

Phe Thr Lys Arg Glu Ser Glu Val Asp Ser Ser Glu Asp Val Gln Leu
        50                  55                  60

Glu Lys Arg Ile Ser Phe Ala Gly Ile Val Ser Ser Ile Ile Asn Gln

```
                65                  70                  75                  80
Leu Pro Ser Ile Ile Gln Ile Ile Gly Asn Ile Ile Lys Ala Gly Leu
            85                  90                  95

Val Lys Arg Asp Asp Ile Asp Asp Ala Phe Ala Leu Val Leu Ala Glu
        100                 105                 110

Tyr Pro His Ile Val Ser Val Phe Glu Asp Ala Phe Gly Asp Phe Thr
        115                 120                 125

Glu Ala Lys Arg Asp Glu Ala Ala Ser Val Gly Thr Gln Ile Leu Gly
        130                 135                 140

Ser Phe Pro Ser Ile Leu Thr Gln Val Val Asn Gly Phe Ser Lys Val
145                 150                 155                 160

Leu Asp Phe Ala Asn Ser Asp Thr Phe Ser Thr Gly Leu Ser Ile Leu
                165                 170                 175

Ser Asn Phe Thr Ser Ile Ala Ser Ser Phe Ala Ser Ser Leu Ser Ser
            180                 185                 190

Val Val Gln Asn Gly Lys Arg Asp Gly Val Glu Asp Ile Val Ser Met
        195                 200                 205

Val Val Arg Gln Ile Pro Asp Leu Ile Val Glu Ala Ser Thr Pro Phe
        210                 215                 220

Val Thr Asn Ala Glu Lys Met Lys Arg Asp Ala Asp Val Ala Ala Ser
225                 230                 235                 240

Leu Val Asp Asn Leu Val Lys Lys Gly Leu Ser Thr Ala Ile Asp Thr
                245                 250                 255

Phe Gly Ala Ala Thr Val Ala Ser Val Val Ser Lys Arg Gln Val Ser
            260                 265                 270

Ser Phe Leu Ser Lys Val Leu Ser Lys Ala
        275                 280

<210> SEQ ID NO 16
<211> LENGTH: 33
<212> TYPE: PRT
<213> ORGANISM: Candida dubliniensis

<400> SEQUENCE: 16

Ser Ile Ile Gly Ile Leu Thr Ala Ile Leu Asn Asn Val Pro Gln Ile
1               5                   10                  15

Ile Asn Val Ile Thr Thr Ile Leu Lys Ser Ile Ile Thr Gly Asn Lys
            20                  25                  30

Arg

<210> SEQ ID NO 17
<211> LENGTH: 32
<212> TYPE: PRT
<213> ORGANISM: Candida tropicalis

<400> SEQUENCE: 17

Ile Ser Phe Ala Gly Ile Val Ser Ser Ile Asn Gln Leu Pro Ser
1               5                   10                  15

Ile Ile Gln Ile Ile Gly Asn Ile Ile Lys Ala Gly Leu Val Lys Arg
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: SYNTHESIZED
<220> FEATURE:
```

```
<221> NAME/KEY: MISC_FEATURE
<222> LOCATION: (2)..(3)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (6)..(6)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (11)..(12)
<223> OTHER INFORMATION: Xaa is Gly, Ser, Thr, Cys, Try, Asn, or Gln
<220> FEATURE:
<221> NAME/KEY: MISC_FEATURE
<222> LOCATION: (13)..(13)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (15)..(15)
<223> OTHER INFORMATION: Xaa is Gly, Ser, Thr, Cys, Try, Asn, or Gln
<220> FEATURE:
<221> NAME/KEY: MISC_FEATURE
<222> LOCATION: (16)..(16)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (18)..(18)
<223> OTHER INFORMATION: Xaa is Gly, Ser, Thr, Cys, Try, Asn, or Gln
<220> FEATURE:
<221> NAME/KEY: MISC_FEATURE
<222> LOCATION: (19)..(19)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Gly, Ser, Thr, Cys, Try, Asn, or Gln
<220> FEATURE:
<221> NAME/KEY: MISC_FEATURE
<222> LOCATION: (24)..(24)
<223> OTHER INFORMATION: Xaa is Ala, Val, Leu, Ile, Pro, Met, Phe, or
      Trp
<220> FEATURE:
<221> NAME/KEY: MISC_FEATURE
<222> LOCATION: (26)..(28)
<223> OTHER INFORMATION: Xaa is any amino acid
<220> FEATURE:
<221> NAME/KEY: MISC_FEATURE
<222> LOCATION: (29)..(30)
<223> OTHER INFORMATION: Xaa is Gly, Ser, Thr, Cys, Try, Asn, or Gln

<400> SEQUENCE: 18

Ser Xaa Xaa Gly Ile Xaa Xaa Xaa Ile Xaa Xaa Xaa Xaa Pro Xaa Xaa
1               5                   10                  15

Ile Xaa Xaa Ile Xaa Xaa Ile Xaa Lys Xaa Xaa Xaa Xaa Xaa Lys Arg
            20                  25                  30
```

PEPTIDES AND BINDING PARTNERS THEREFOR

The present invention relates to moieties selected from a specific type of peptide and binding partners such as antibodies therefor, which have applications in diagnosis and therapy. Methods for using these moieties in diagnosis and therapy as well as in processes for screening for therapeutic compounds are also part of the invention. The isolated peptide and specific binding partners therefor are novel and form further aspects of the invention.

BACKGROUND TO THE INVENTION

*Candida* species are the most common fungal pathogens of humans and the causative agents of oral, gastrointestinal and vaginal candidiasis, giving rise to severe morbidity in millions of individuals worldwide. Vaginal candidiasis affects ~75% of women at least once during fertile age, equating to ~30 million infection episodes/year (3× more than tuberculosis and 8× more than HIV: WHO 2007). *Candida* infections are also the $3^{rd}$ most common hospital-acquired bloodstream infection, making *Candida* species more medically-important than most bacterial infections including Enterococci (*E. coli*) and *Pseudomonas* spp. Systemic candidiasis is fatal (30-50% mortality) with 300,000 cases/year of candidaemia, equating to 100,000 deaths/year. Furthermore, *Candida* infections are the most common oral manifestation of HIV infection, with 50% of HIV+ patients and 90% AIDS patients suffering from oral candidiasis. With ~4 million cases of HIV/year, this equates to ~2 million oral candidiasis cases/year. Indeed, one of the biggest killers of the immunocompromised population is fungal infection. In the USA, yearly healthcare costs for fungal infections are $2.6 billion, of which *Candida* infections account for $1.8 billion. EU healthcare costs are estimated to be similar. Therefore, *Candida* pathogens carry an immense health burden and represent a major socio-economic challenge for worldwide communities.

*Candida albicans* is a member of the normal human microbiome. Although typically a commensal of the oral cavity, gastrointestinal and urinogenitary tracts, *C. albicans* is also an extremely frequent cause of superficial infections such as vaginitis. Moreover, common iatrogenic procedures, such as gastrointestinal surgery, implantation of a central venous catheter or antibiotic treatment are major risk factors for disseminated candidiasis. This form of systemic candidiasis is now the third most common cause of nosocomial bloodstream infections and the mortality of severe sepsis caused by *Candida* species is over 50% in some patient groups.

Identifying new epithelial and fungal targets that stimulate protective host immunity will ultimately have major implications for global health.

*C. albicans* virulence relies on a number of factors, including morphological plasticity, the expression of adhesins and invasins, robust stress responses, immune evasion, metabolic flexibility and nutrient acquisition. However, it remains unclear, how *C. albicans* causes damage.

The mechanisms by which *C. albicans* damages host cells have been considered to be multi-factorial, and presumed to rely on a combination of adhesion, invasion, hyphal extension, turgor pressure and the secretion of hydrolytic enzymes. Although toxin production by *C. albicans* has long been postulated and the culture supernatants of *C. albicans* hyphae shown to exhibit haemolytic activity, the mechanism underlying *C. albicans* ability to lyse host cells has remained elusive. It is clear, however, that hyphae are essential for adhesion, invasion and damage. Thus, damage is caused by hyphae and/or a hyphal associated factor.

The gene ECE1 (extent of cell elongation 1) was first identified two decades ago due to its heightened expression during hypha formation. However, deletion of ECE1 did not affect hypha formation in *C. albicans* and phenotypic differences between *C. albicans* wild type and ECE1 deletion strains have not been reported. Despite this, ECE1 expression has been used as a marker for hypha formation in multiple independent studies and ECE1 is one of the most strongly expressed genes during hyphal formation. In fact, ECE1 is within a small group of core hyphal associated genes. It has previously been reported that recombinant Ece1 is processed by the protease, Kex2, at lysine/arginine residues. However, the function of Ece1 has never been shown.

Currently, the gold standard for treating fungal infections is the use of antifungal drugs, which predominantly target either the cell wall (echinocandins), cell membrane (polyenes) or ergosterol synthesis (azoles). However, the continuing increase in *Candida* infections together with increasing drug resistance highlights the need to discover new and better agents that target either (i) epithelial processes that recognise and normally restrict these potentially life-threatening pathogens to mucosal surfaces or (ii) fungal determinants that promote infection and/or mediate immune activation and protective immunity. Despite this, there are no vaccine candidates or immune-based intervention strategies for combating *Candida* infections. Likewise, there are no commercial drugs that specifically target mucosal fungal infections.

SUMMARY OF THE INVENTION

The applicants have found that Ece1 plays a key role in host cell activation and damage, as demonstrated by the fact that deletion of ECE1 renders *C. albicans* unable to damage or activate inflammatory responses in human epithelial cells. Moreover, the applicants have demonstrated that a single peptide product of proteolytic processing of Ece1 acts as a peptide toxin, in particular, a pore-forming toxin: the first such described in a human fungal pathogen. By targeting this single peptide it is possible to prevent both host damage (fungus driven) and manipulate immunity to induce protection (host driven). To date, no other *Candida* protein exhibits these phenotypes and no other approach can address both fungal and host aspects.

This gives rise to a number of diagnostic and therapeutic applications for this peptide and also for specific binding partners for it, as well as for the discovery and development of anti-fungal compounds that target this specific peptide.

According to a first aspect of the present invention there is provided an optionally labelled peptide comprising SEQ ID NO 1

```
                                              (SEQ ID NO. 1)
            SIIGIIMGILGNIPQVIQIIMSIVKAFKGNKR
``` or a variant thereof, or an immunogenic fragment of either of these; or a labelled form thereof.

As used herein, the expression 'variant' refers to a peptide sequence in which the amino acid sequence differs from the sequence of SEQ ID NO 1 in that one or more amino acids within the sequence are substituted for other amino acids. However, the variant produces a biological effect which is similar to that of SEQ ID NO 1. In particular, any variant will interact with the surface receptor EGFR (epidermal growth factor receptor) to give rise to activation of an immune response and/or immunoglobulins and in particular antibodies that are produced in response to said variants will cross-react with SEQ ID NO 1. Alternatively or additionally, the variant will be damage inducing in host cells, for example by acting as pore forming agents.

Amino acid substitutions may be regarded as "conservative" where an amino acid is replaced with a different amino acid in the same class with broadly similar properties. Non-conservative substitutions are where amino acids are replaced with amino acids of a different type or class. Amino acid classes are defined as follows:

| Class | Amino acid examples |
|---|---|
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions may also be possible provided that these do not interrupt the function of the peptide and in particular its ability to cross-react with immunoglobulins that react with SEQ ID NO 1.

Broadly speaking, fewer non-conservative substitutions will be possible without altering the biological activity of the polypeptides.

Figure 2:
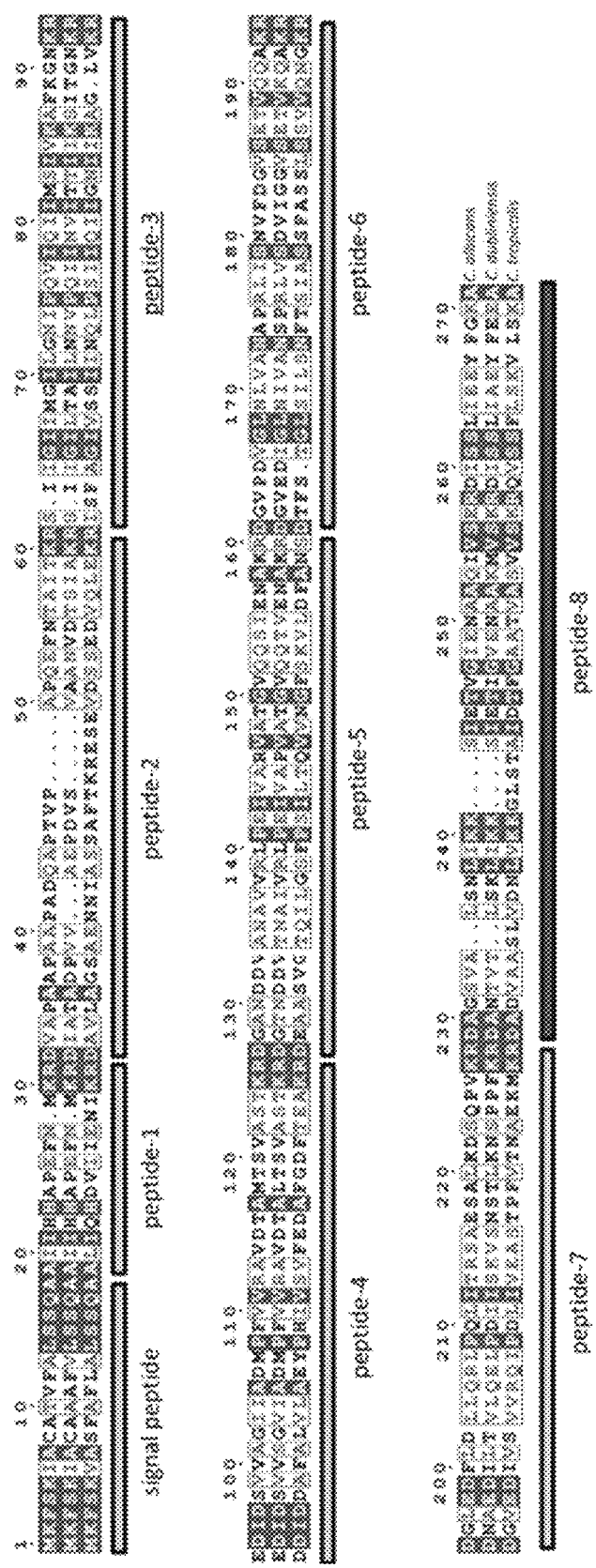

Particular variants may include peptides encoded by orthologues or paralogues of the gene sequence that encodes the peptide of SEQ ID NO 1 in *C. albicans*. Particular variant sequences are orthologues from *C. dubliniensis* and *C. tropicalis* as shown in FIG. 2 hereinafter.

In general, variants will have amino acid sequences that will be at least 70%, for instance at least 71%, 75%, 79%, 81%, 84%, 87%, 90%, 93% or 96% identical to SEQ ID NO 1. Identity in this context may be determined using the BLASTP computer program with SEQ ID NO 1 as the base sequence. The BLAST software is publicly available at blast.ncbi.nlm.nih.gov/Blast.cgi (accessible on 12 Mar. 2009).

Variants may also include addition sequences such as tag sequences that may be used for instance in facilitating purification of the peptide or in detection of it. Thus for instance, the variant may further comprise an affinity tag such as chitin binding protein (CBP), maltose binding protein (MBP), glutathione-S-transferase (GST), FLAG, myc, biotin or a poly(His) tag as are known in the art. In another embodiment, the variant may comprise a fluorescent protein such as green fluorescent protein (GFP).

When the peptide is for use in diagnostics or screening of anti-fungal proteins, it may be helpful to label the peptide, for example with a chemical label such as a fluorescent or radiolabel. There are a wide range of such labels available commercially, but examples include fluorescein and derivatives such as fluorescein isothiocyanates (FITC), carboxy-fluorescein succinimidyl esters, fluorescein dichlorotriazine (DTAF) and 6-carboxy-4',5'-dichloro-2',7'-dimethoxyfluorescein (JOE), rhodamine and derivatives such as carboxytetramethylrhodamine (TAMRA), tetramethylrhodamine (TMR) and its isothiocyanate derivative (TRITC), sulforhodamine, Texas Red, Rhodamine Red and the dyes available under the trade name Alexa.

These labels may be incorporated into the peptide using conventional methods.

The term "fragment" as used herein refers to any portion of the amino acid sequence of SEQ ID NO 1 which has biological function in common with SEQ ID NO 1. (e.g. damage-inducing, immunomodulatory or is immunogenic, for instance an epitopic fragment) and which reacts with specific binding partners for SEQ ID NO 1. Fragments may comprise more than one portion from within the full-length protein, joined together. Portions will suitably comprise at least 5 and preferably at least 10 consecutive amino acids from the basic sequence. Suitable fragments will include deletion mutants comprising up to 31 amino acids, for example at least 7 amino acids, such as at least 10, for instance at least 15, such as at least 20, more suitably at least 30 amino acids.

Notably, SEQ ID NO 1 includes two segments that contain sequences with high amyloidogenic potential (underlined), which may be involved in cell interactions and activation due to their hydrophobic nature and ability to potentially form α-helices. Particular variants or fragments of SEQ ID NO 1 will contain at least one of said sequences which are represented below as SEQ ID NO 2 and SEQ ID NO 3 respectively.

```
                                          (SEQ ID NO. 2)
            IIGIIMGIL (SEQ ID NO. 3)
            QVIQIIMSIV
```

In a particular embodiment however, the peptide is a peptide of SEQ ID NO. 1. The peptide is in isolated or purified form and in particular is free of at least some and preferably all other peptides obtainable by Kex2 protease cleavage of the Ece1 protein of *C. albicans*. Although the peptide may be isolated from *C. albicans* that has been subject to Kex2 protease digestion, in a particular embodiment, the peptide is prepared synthetically using conventional preparation methods.

As discussed above, peptides of the invention and in particular the peptide of SEQ ID NO 1 has been found to be immunogenic. Thus in a second aspect of the present invention there is provided a specific binding partner for a peptide as described above; or a labelled form thereof. Particular specific binding partners are immunoglobulins, such as an antibody or a binding fragment thereof. Examples of suitable binding fragments of antibodies include Fab, Fab', F(ab)2, F(ab')2 and FV, VH and VK fragments.

Antibodies may be polyclonal or monoclonal but in a particular embodiment, the antibodies are monoclonal antibodies.

Antibodies can be prepared using conventional methods involving inoculation of an animal such as mouse or guinea pig with a peptide of the first aspect of the invention and harvesting antibodies from the blood thereof. Monoclonal antibodies can be obtained therefrom by fusing antibody producing cells such as spleen cells from the inoculated animal with a hybridoma cell, culturing this cell and harvesting monoclonal antibodies therefrom.

Where the antibody is used in diagnostic or screening applications, it may be chemically labelled to facilitate detection. Suitable labels will be similar to those described above for the peptides of the invention. However, the antibody may be detectable using a secondary antibody which is modified so as to be detectable using a development reaction, for example because it includes an enzymatic label, as is conventional in the art.

The peptide of the invention has therapeutic applications. Therefore, a third aspect of the invention provides a peptide as described above for use in therapy, and in particular for the treatment or prevention of infection by *Candida albicans*. In particular, the therapy is for the treatment or prevention of oral, gastrointestinal or mucosal and in particular vaginal infection by *Candida albicans*.

In order to achieve these therapeutic effects, a non-toxic amount of a peptide as described above or a pharmaceutically acceptable composition comprising it is administered to a subject, such as a human or animal. The non-toxic amount is sufficient to produce an immune response that is protective against *C. albicans* infection. Thus the peptide may be used as a vaccine in a vaccination method. Such a method forms a fourth aspect of the invention.

The amount of peptide administered will vary depending upon factors such as the size and health of the patient, the nature of the condition being treated etc. in accordance with normal clinical practice. Typically, a dosage in the range of from 1 µg-50 mg/Kg such as from 1-50 µg/Kg but in particular from 1-50 mg/Kg, for instance from 2-20 mg/Kg, such as from 5-15 mg/Kg would be expected to produce a suitable immune response. Since the peptide of SEQ ID NO 1 has been found to have cytotoxic effects however, care must be taken to ensure that the dosage is sufficient to prime the immune system but not cause unwanted toxic side effects.

One way of avoiding such side effects is to use a variant or fragment of the peptide of SEQ ID NO 1 in the fourth aspect of the invention. As described hereinbelow, the applicants have found that full length peptide of SEQ ID NO 1 is capable of inducing cellular lysis and stimulation of the inflammatory response in epithelial cells. These side effects may therefore be avoided by using a variant sequence which is immunogenic, or a fragment of SEQ ID NO 1, in particular one which contains at least SEQ ID NO 2 or SEQ ID NO 3 as described above. Furthermore, the applicants have found that the peptide of SEQ ID NO 1 interacts with phospholipids, omission of the dibasic (lysine, arginine) C-terminal head of the peptide may mitigate any unwanted toxic effects.

An alternative way of avoiding unwanted side effects is to use the specific binding partners and in particular the antibodies of the second aspect of the invention in a passive immunisation regime. Thus in a fifth aspect of the invention, there is provided a specific binding partner for a peptide as described above for use in therapy, in particular where the therapy is the treatment or prevention of infection by *Candida albicans*.

As before, in order to achieve these effects, an effective amount of the specific binding partner and in particular the antibody, or a pharmaceutical composition containing it is administered to a subject in need thereof. Thus the specific binding partner may be used as a vaccine in a vaccination method that may be prophylactic or therapeutic. Such a method forms a sixth aspect of the invention.

Again, the amount of specific binding partner administered will vary depending upon factors such as the size and health of the patient, the nature of the condition being treated etc. in accordance with normal clinical practice. Typically, a dosage in the range of from 1 to 50 mg/Kg, for instance from 2-30 mg/Kg such as from 5-10 mg/Kg would produce a suitable therapeutic or protective effect.

For administration to subjects, the peptide or its specific binding partner is suitably administered in the form of a pharmaceutical composition. Thus a seventh aspect of the invention provides a pharmaceutical composition comprising a peptide as described above and a pharmaceutically acceptable carrier.

An eighth aspect of the invention provides a pharmaceutical composition comprising a specific binding partner for a peptide as described above and a pharmaceutically acceptable carrier.

Suitable pharmaceutical compositions will be in either solid or liquid form. They may be adapted for administration by any convenient route, such as parenteral, oral, vaginal or topical administration or for administration by inhalation or insufflation. The pharmaceutical acceptable carrier may include diluents or excipients which are physiologically tolerable and compatible with the active ingredient.

Parenteral compositions are prepared for injection, for example either subcutaneously or intravenously. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories or intranasal aerosols. For suppositories, traditional binders and excipients may include, for example, polyalkylene glycols or triglycerides; such suppositories may be formed from mixtures containing the active ingredient.

Peptides of the first aspect and specific binding partners of the second aspect of the invention, may, if required, be produced using recombinant methods. For this purpose, nucleic acids that encode either the peptide or specific binding partner are prepared and these form a ninth aspect of the invention.

Such nucleic acids may be incorporated into a suitable expression vector or plasmid, which is then used to transform a cell and in particular a prokaryotic cell. A suitable nucleic acid that encodes the peptide of SEQ ID NO 1 may correspond to a nucleic acid sequence that occurs naturally in strains of *C. albicans* strains. However, in a particular embodiment, the nucleic acid is designed so that it is 'codon optimised' for the expression host being used in the recombinant production method. This should ensure efficient and effective production. The design and preparation of such nucleic acids will be apparent to the skilled person using techniques conventional in the art.

A recombinant cell that has been transformed with such a nucleic acid forms a tenth aspect of the invention.

Suitable cells will be conventional expression hosts such as *E. coli* and *Pichia pastoris* An eleventh aspect of the invention provides a method for producing a peptide as described above, or a specific binding partner therefor, which method comprises culturing a recombinant cell as described above and recovering said peptide or specific binding partner therefrom.

However, the peptides of the first aspect and the specific binding partners of the second aspect of the invention may also be useful in diagnosis of pathogenic invasive *C. albicans* infection. *C. albicans* forms part of the commensal flora and so may be found in most individuals at low levels, for example of up to 800 organisms per ml sample. However, as discussed previously, invasive or pathogenic infections may arise, in particular in immunocompromised individuals, and in such cases, the level of *C. albicans* increases dramatically or there is 'overgrowth'. Although in many cases, pathogenic invasive oral or vaginal infection of *C. albicans* produces visible symptoms, it would be helpful if tests could be provided that allow for early diagnosis of such infection as this will allow treatment to be started before the infection escalates to a more dangerous systemic infection, or for the diagnosis of invasive pathogenic infection in organs which may not be examined easily such as the intestine.

In an eleventh aspect of the invention, there is provided a method for diagnosis of pathogenic invasive infection by *C. albicans*, said method comprising contacting a sample from an individual with a peptide as described above or a specific binding partner therefor, and detecting whether the sample contains moieties that interact with said peptide or specific binding partner at a sufficient level to indicate a pathogenic invasive infection.

Detection of high levels of the peptide of the invention and in particular a peptide of SEQ ID NO 1 in a sample may be indicative of an overgrowth of *C. albicans* in the individual, leading to the symptoms of candidiasis. This may be determined by using a specific binding partner for the peptide to capture it. The specific binding partner is suitably either directly or indirectly labelled so as to detect or visualise the peptide in a quantitative or semi-quantitative manner.

Similarly, an elevated level of specific binding partner, and in particular, antibodies to the peptide of SEQ ID NO 1 present in the sample can also indicate that an overgrowth of *Candida* has occurred and that pathogenic invasive infection may result. In this case, the diagnostic method will typically utilise a peptide of the invention to bind with antibodies in the sample. The peptide may be immobilised or labelled to assist in the capture and/or detection of the antibodies in the sample.

The sample used in the method may be any suitable biological sample including a blood, serum, sputum, saliva or mucosal swabs for instance oral or vaginal swabs, but may also include biopsy samples such as intestinal tissue samples.

The levels of peptide or specific binding partner that is indicative of a pathogenic invasive infection or *Candida* 'overgrowth' rather than the presence of a non-damaging commensal species will vary depending upon factors such as the nature of the sample and the particular patient being examined and the particular technique used to carry out the assay, but will generally be determinable in a particular case in accordance with conventional clinical techniques. Typically however, levels of *C. albicans* of up to about 800 cells/ml saliva sample may be acceptable as a commensal background, but levels significantly higher than this, in particular at least an order of magnitude greater than this, can be indicative of overgrowth and pathogenic invasive infection. Detection of levels of the peptide of the invention at levels that equate to this cellular population of *Candida* species would be a cause for concern.

Methods include those conventionally known in the art such as immunoassays, for instance, enzyme-linked immuno sorbent assays (ELISA) but may also include multiplex bead assays, immunohistochemistry or immunofluorescence. Such methods are well known in the art.

Kits for carrying out such methods form a further aspect of the invention. Thus the invention further provides a kit for diagnosing a pathogenic invasive infection by *C. albicans*, said kit comprising a peptide as described above or a specific binding partner therefor, and means for detecting complexes formed between said peptide or specific binding partner and moieties in the sample. The nature of the detection means will vary depending upon the particular technique being employed. In general, detection means will include label means. The label means is suitably one in which the intensity of the signal developed can be related to the concentration of the moiety being detected as this will allow a distinction to be made between levels of *C. albicans* which is commensal and a level at which disease may result.

Suitable label means may be indirect label means which allow signals to develop following a subsequent reaction such as a chemical reaction. These will include enzymatic labels such as peroxidase labels and in particular horseradish peroxidase. Alternatively, labels may include direct labels such as visible plastic labels, fluorescent labels like fluorescein or derivatives thereof, rhodamine or derivatives as described above, as well as radiolabels such as $^{125}$I labels. The labels may be bound to or otherwise associated with the peptide of the invention or the specific binding partner therefor, or they may be linked to a secondary detection moiety such as a secondary antibody or other binding moiety. The precise form the detection means will take will vary depending upon the detection technique employed.

For instance for immunoassays such as ELISA assays, detection means may include solid supports such as 96-well plates or beads that may be ferromagnetic in nature. In such cases, the solid supports will generally have binding moieties for either the peptide of the first aspect or the specific binding partner of the second aspect immobilised thereon.

Where the binding moieties are specific for the peptide of the invention, for instance they are specific binding partners of the second aspect of the invention, incubation of the sample in contact with the solid support will result in capture of the peptides on the support. Once the sample has then been removed from the support for example by washing, the presence of immobilised peptide can be detected by application of a secondary detection antibody that also binds the peptide but carries a label which is either directly or indirectly detectable. Directly detectable labels may comprise visible labels such as fluorescent or radiolabels as described above. Indirect labels may be detected in subsequent reactions such as horseradish peroxidase that is carried by the secondary detection antibody or by a tertiary detection antibody that binds to the immobilised secondary antibody.

Similarly where the binding moieties on the solid support specific for a specific binding partner and in particular an antibody to the peptide of the invention, they will generally comprising a peptide of the first aspect of the invention. In this case, incubation of the sample in contact with the solid support will result in capture of antibodies to the peptide on the support. Once the sample has then been removed from the support for example by washing, the presence of immobilised antibody can similarly be detected by application of a secondary detection antibody that binds the antibody but carries a label which is either directly or indirectly detectable.

For immunohistochemical or immunofluorescence detection methods, kits will suitably contain labelled reagents such as suitable stains or dyes that are targeted to the required moiety and in particular the peptide of the invention, as a result of attachment to a suitable specific binding partner. In use, the sample will be prepared in the usual way. In particular, a tissue sample is collected, if necessary sectioned and fixed onto a support such as microscope slide whereupon the labelled reagent is administered to the slide so as to visualise the target moiety and in particular the peptide of SEQ ID NO 1. The kit may comprise one or more additional elements used in immunohistochemical or immunofluorescence method. These include the slide itself, fixing agent such as paraformaldehyde, detergent such as Triton® detergent for reducing surface tension and facilitating coverage by the labelled reagent, and blocking agents to reduce background signal caused by non-specific binding of the labelled reagent, which blocking agents may include serum, bovine serum albumin or gelatin.

In addition, since the peptide of SEQ ID NO 1 has been identified as a cytotoxic element in C. albicans infections, it can be used to develop drugs and other therapies that specifically target this peptide. It may therefore form a useful tool in the screening of antifungal compounds. Screening methods of this type form a further aspect of the invention.

Screening methods may take a variety of forms. Typically however, compounds under test will be contacted with a peptide of the invention and in particular a peptide of SEQ ID NO 1 and any interaction between the peptide and the compound will be monitored. The interaction may take place in a vessel or well for instance of a 96-well plate, and the interaction detected using for example, a change in reflectance of polarised light caused by binding. Alternatively, the interaction may take place at a surface at which one of the peptide or the target reagent is immobilised and under conditions where interaction may be detected using techniques such as surface plasmon resonance and the like.

DETAILED DESCRIPTION OF THE INVENTION

The invention will now be particularly described by way of example with reference to the accompanying diagrams which are summarised as follows. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Figure 1B:
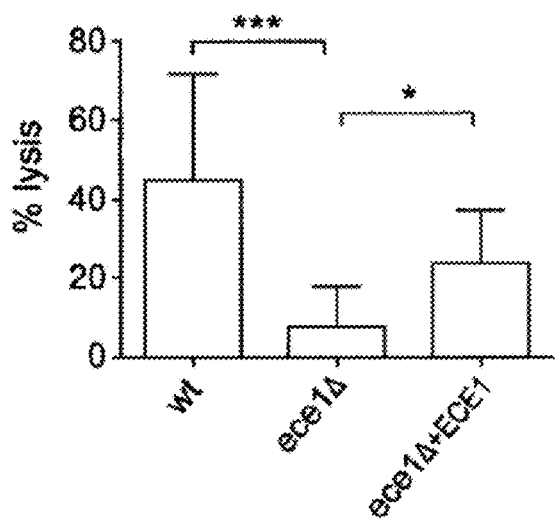
Figure 1C:
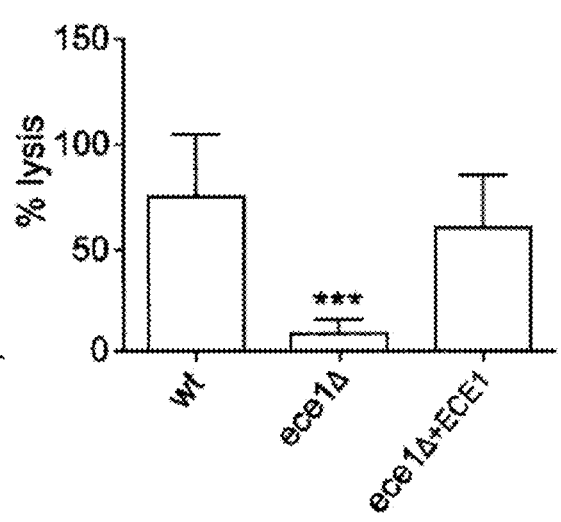

FIG. 1A-C is a series of graph showing the results of an experiment to determine whether ECE1 is required for damage of a variety of host cells. Oral TR146 (FIG. 1A), gastrointestinal Caco (FIG. 1B) and vaginal (FIG. 1C) epithelial cells were infected with C. albicans wild type (wt), ece1Δ or ece1Δ/Δ-ECE1 strains for 24 hours and damage assayed by LDH release as described below.

FIG. 2 shows the structure of Ece1 and phylogeny with other species. It shows the alignment of Ece1 from C. albicans (SEQ ID NO 13) and orthologues in C. dubliniensis (SEQ ID NO 14) and C. tropicalis (SEQ ID NO 15) (which are the only three sequenced fungal species that encode Ece1). The bars below the alignment indicate that the peptides resulted from Kex2 digestion of the CaEce1. Only peptide 3 of C. albicans and C. dubliniensis form transmembrane α-helical structures.

FIG. 3A-C is a series of graphs showing the results of an experiment to demonstrate that a peptide of the invention is sufficient to lyse host epithelial cells. Mixtures of Ece1 peptides at different concentrations or the peptide of SEQ ID NO 1 alone were added to TR146 oral epithelial cells in the presence of the ece1Δ mutant, incubated for 24 hours and damage assessed by measuring LDH release (FIG. 3A). Subsequently the different Ece1 peptides were added alone (without C. albicans cells) to TR146 (FIG. 3B) and vaginal A431(FIG. 3C) epithelia, incubated for 24 hours and damage assessed by measuring LDH release as described below.

Figure 4:
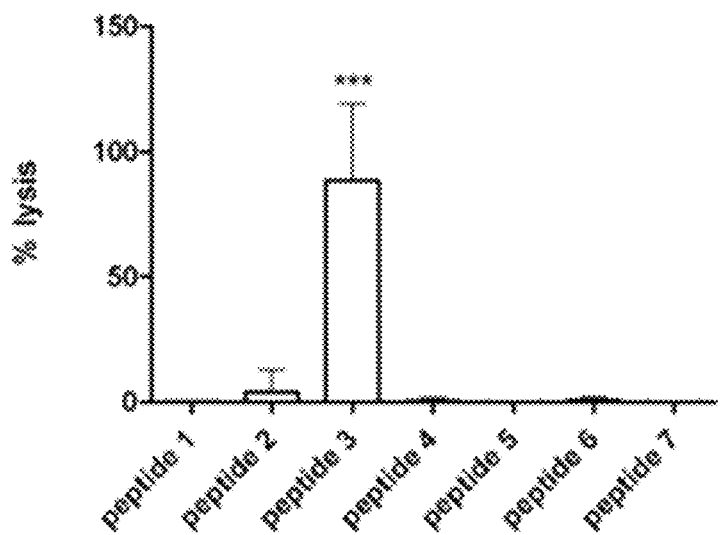

FIG. 4 is a graph showing the results of an experiment to determine which of the Ece1 peptides are haemolytic toxins where the peptide of SEQ ID NO 1 is peptide 3. Individual peptides were incubated with human erythrocytes for 1 hour and heamolysis assayed by measuring haemoglobin release (as measured by absorbance at 541 nm, normalised to a 100% lysis control).

Figure 5A:
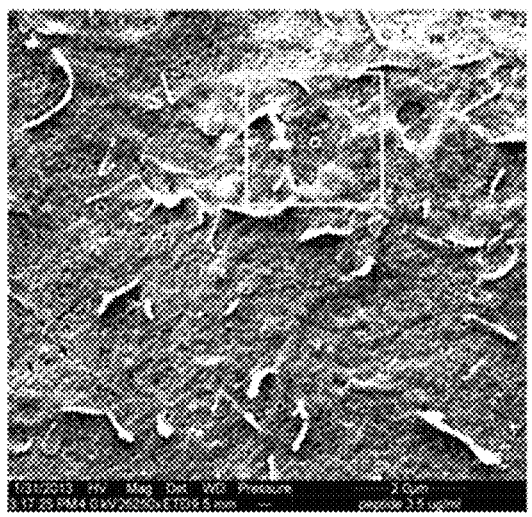

FIG. 5A,B shows the results obtained by scanning electron microscopy of an experiment to determine whether the peptide of SEQ ID NO 1 forms pores in epithelial membranes. Oral epithelial (TR146) monolayers were incubated with 5 μg/ml peptide 3 (SEQ ID NO 1) for 5 hours and pore formation assessed by scanning electron microscopy. FIG. 5 shows a further magnified view of a region indicated in FIG. 5.

Figure 6A:
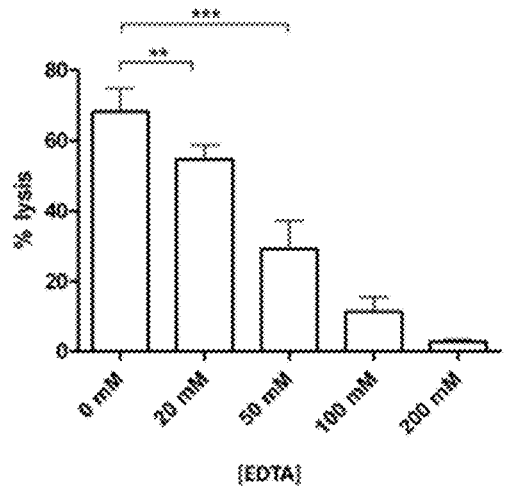
Figure 6B:
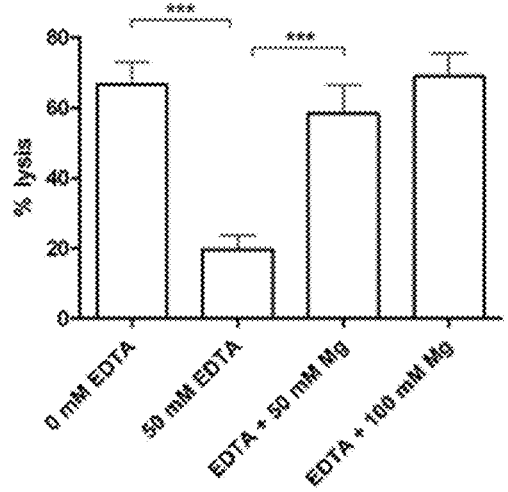

FIG. 6A,B is a series of graphs showing the results of an experiment to demonstrate that the haemolytic activity of the Ece1 peptide 3 of SEQ ID NO 1 is ion-dependent. The peptide was incubated with human erythrocytes with increasing concentrations of the divalent cation chelator EDTA (FIG. 6A) and haemolysis assayed by measuring haemoglobin release (absorbance at 541 nm, normalised to a 100% lysis control). The inhibitory effect of 50 mM EDTA was reversed by the addition of 50 or 100 mM magnesium (FIG. 6B).

Figure 7A:
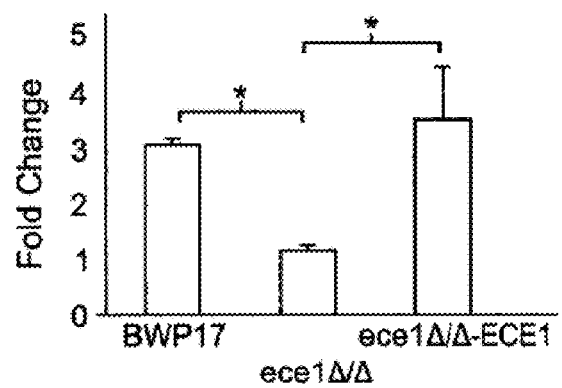
Figure 7B:
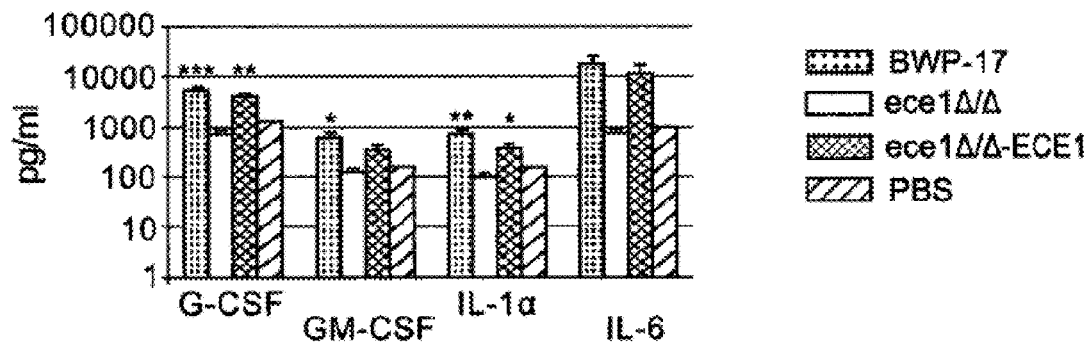

FIG. 7A,B is a series of graphs showing the results of experiments to investigate whether the peptide of the invention activates epithelial immunity and cFos. (FIG. 7A) Induction of c-Fos DNA binding activity in TR146 epithelial cells after 3 hours infection with ece1Δ/Δ null mutant, ece1Δ/Δ-ECE1 revertant and the BWP17 parent strain. (FIG. 7B) Production of cytokines by TR146 epithelial cells after 24 hour infection with ece1Δ/Δ null mutant, ece1Δ/Δ-ECE1 revertant, the BWP17 parent strain or uninfected cells. Data shown are the mean of 3 independent experiments. Error bars show SEM. *=p<0.05, =p<0.01, *=p<0.001.

Figures 8A, 8B, 9:
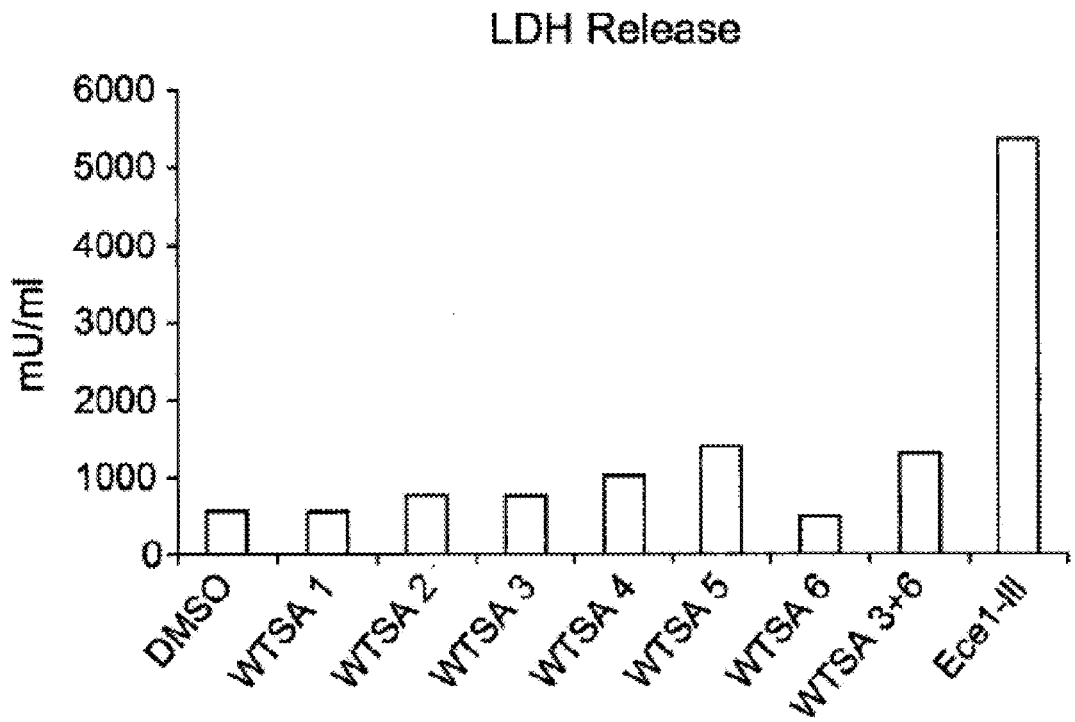
Figure 10A:
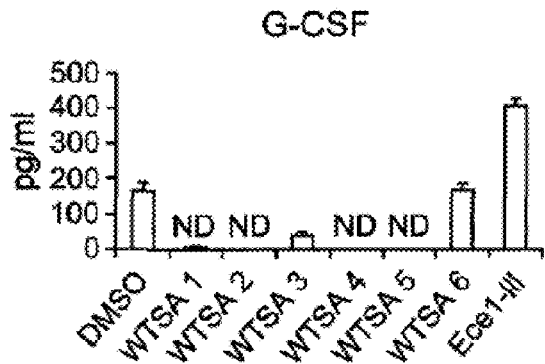
Figure 10B:
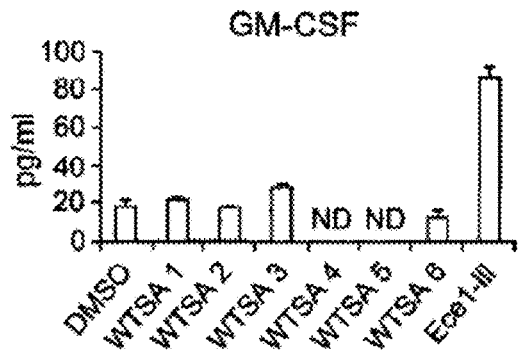
Figure 10C:
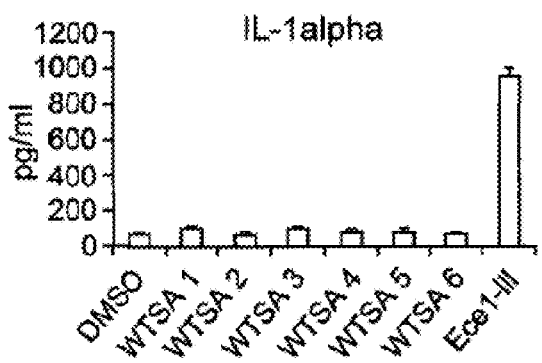
Figure 10D:
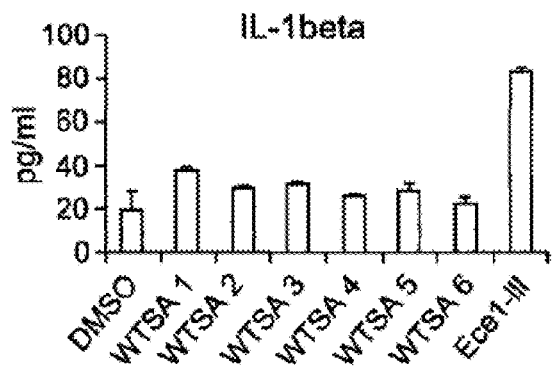
Figure 10E:
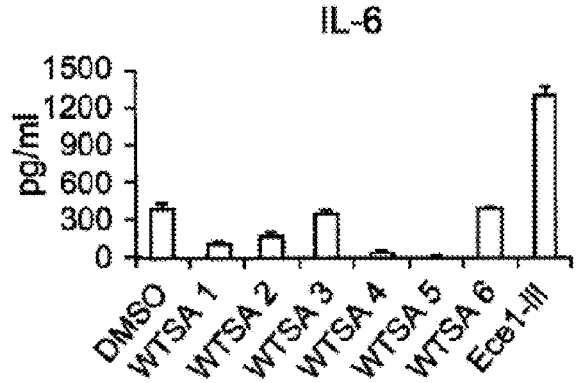

FIG. 8A,B shows the amino acid sequences of Ece1-III and WTSA peptides where FIG. 8A shows the amino acid sequence of Ece1-III (SEQ ID NO 1). Amyloidogenic regions are shown in bold type; and FIG. 8B shows the amino acid sequences of WTSA peptides. Each individual WTSA peptide constitutes a partial fragment of full length Ece1-III. Amyloidogenic regions are shown in bold type.

FIG. 9 is a graph showing the results of analysis of WTSA peptide-induced damage to TR146 oral epithelial cells.

Individual WTSA peptides (250 µg/ml) and WTSA 3 in combination with WTSA 6 (both peptides at 250 µg/ml) were added to confluent monolayers of TR146 oral epithelial cells and incubated for 24 hours at 37° C., 5% $CO_2$. Following incubation, growth medium was removed and assayed for the presence of lactate dehydrogenase (LDH), a surrogate marker of cellular lysis. Dimethyl sulfoxide (DMSO) was used as a vehicle only (negative control). Full length Ece1-III (250 µg/mL) was used as the positive control.

FIG. 10A-E shows WTSA peptide-mediated activation of immune responses in TR146 oral epithelial cells. WTSA peptides 1-6 were added to confluent monolayers of TR146 oral epithelial cells at a final concentration of 250 µg/mL and incubated for 24 hours at 37° C., 5% $CO_2$. Following incubation, growth medium was removed and secreted immunostimulatory cytokines were quantified by multiplex bead assay. Concentration of detected cytokines was expressed as picograms per milliliter (pg/mL). ND=not detected.

Figure 11A:
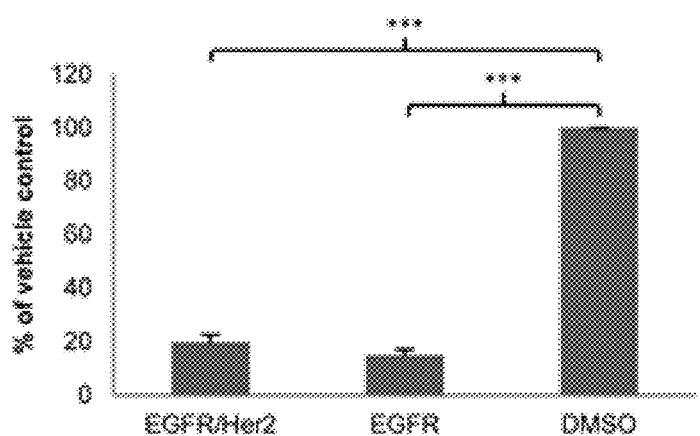
Figure 11B:
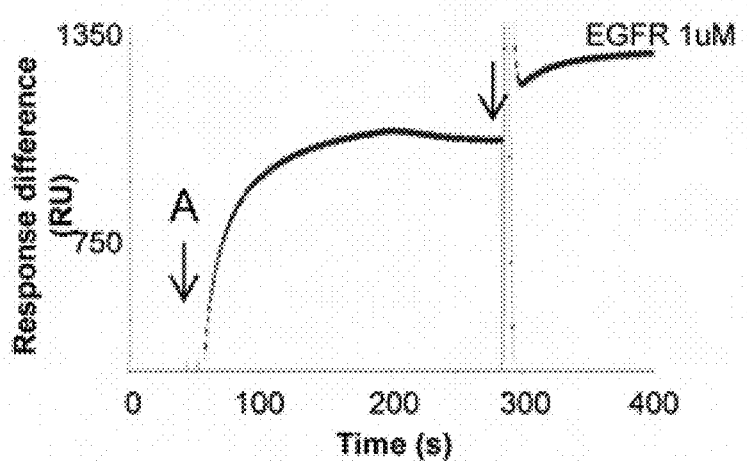
Figure 11C:
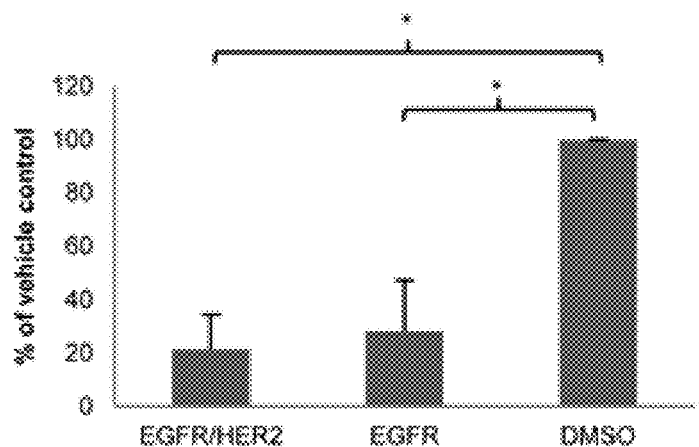

FIG. 11A-C is a series of graphs showing the results of experiments to investigate whether the peptide of the invention binds EGFR and activates c-Fos. (FIG. 11A) Induction of c-Fos DNA binding activity in TR146 epithelial cells after 3 hours infection with wild-type C. albicans cells, which were pre-treated for 1 hour with 4 µM GW2974 (EGFR/Her2 inhibitor), 1 µM PD153035 (EGFR inhibitor) or DMSO (vehicle control). (FIG. 11B) Sensorgram of fluid phase EGFR binding to immobilised Ece1-III of SEQ ID NO 1 demonstrating high affinity binding. Injection of fluid phase components was at point A. (FIG. 11C) Induction of c-Fos DNA binding activity in TR146 epithelial cells after 3 hours infection with Ece1-III, which were pre-treated for 1 hour with 4 µM GW2974 (EGRF/Her2 inhibitor), 1 µM PD153035 (EGFR inhibitor) or DMSO (vehicle control). Data shown are the mean of 2(A) or 3 (C) independent experiments. Error bars show SEM. *=p<0.05, =p<0.01, *=p<0.001.

Figure 12A:
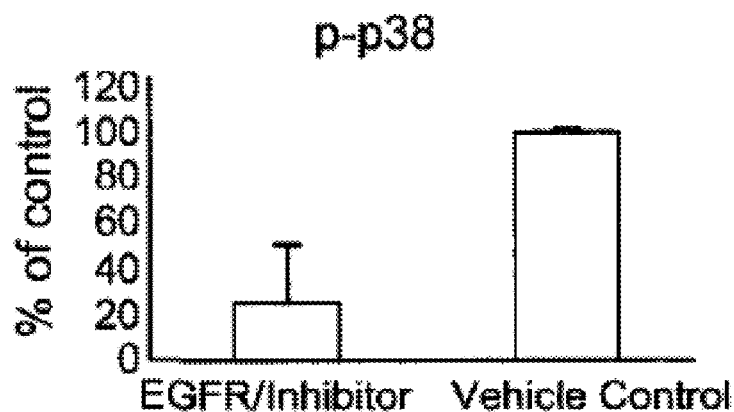
Figure 12B:
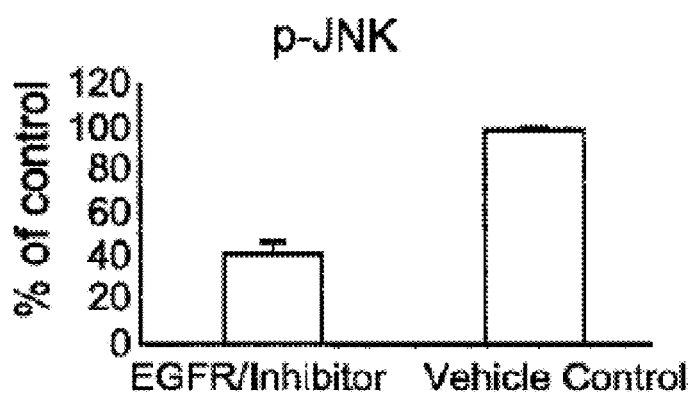
Figure 12C:
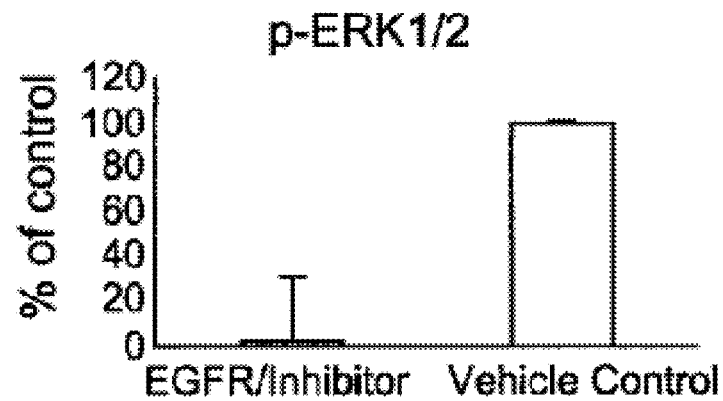

FIG. 12A-C is a set of graphs showing the effect of EGFR inhibition on epithelial cell signalling. Blocking EGFR signalling in oral epithelial cells (TR146) with Gefitnib (10 µM) inhibits the activation of MAPK intracellular signalling in cells treated with Ece1-III (50 µg/mL) for 2 hours as measured by decreases in levels of phosphorylated p38, JNK and ERK1/2 relative to the vehicle control (DMSO).

Figure 13:
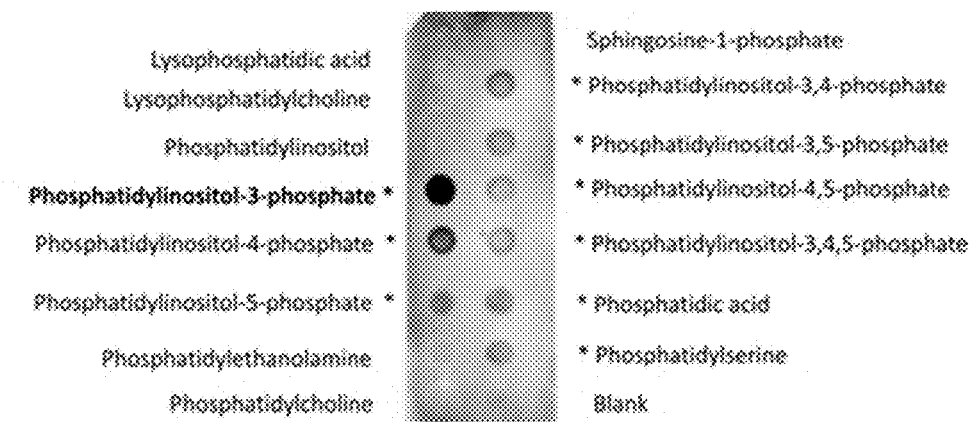

FIG. 13 shows the results of an assay to detect Ece1-III-phospholipid interactions. Ece1-III was used to probe a phospholipid array (PIP Strip membrane). Binding was assessed by hybridisation with anti-Ece1-III antibody, followed by detection with anti-rabbit antibody conjugated to horse radish peroxidase.

Figure 14A:
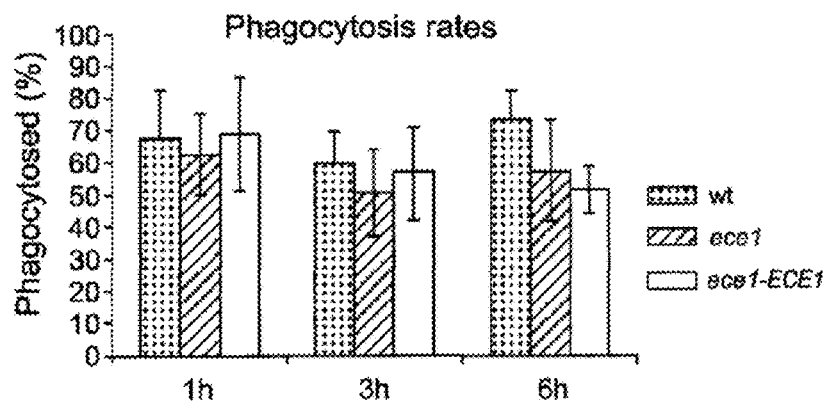
Figure 14B:
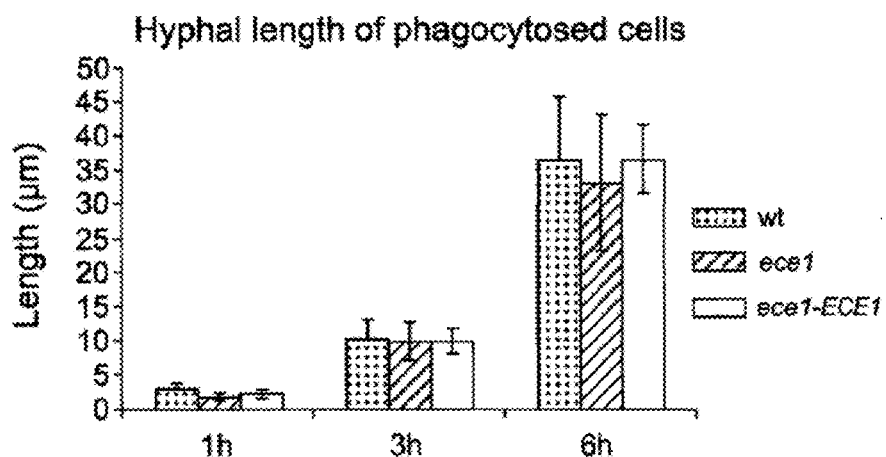
Figure 14C:
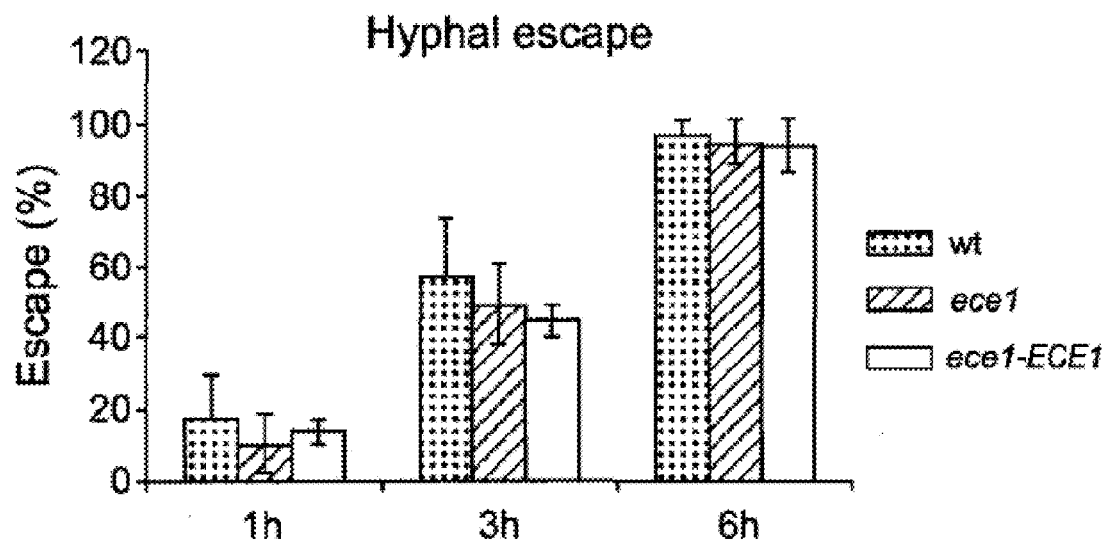

FIG. 14A-C is a series of graphs showing the results of an experiment to determine C. albicans-macrophage interactions. C. albicans strains were incubated with RAW264.7 macrophages for indicated times and the following parameters determined: (FIG. 14A) The number of phagocytosed fungal cells as a percentage of total number of fungal cells; (FIG. 14B) Hyphal length; (FIG. 14C) The percentage of outgrowing hyphae compared to the total number of internalised yeast mother cells.

Figure 15:
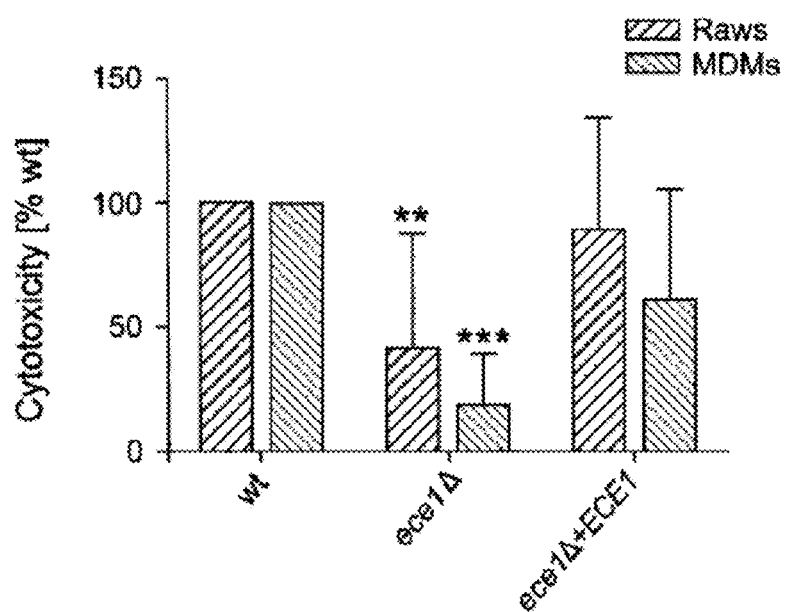

FIG. 15 is a graph showing the results of an experiment to show that ECE1 is required for damage of macrophages. Indicated macrophage cell types were co-incubated with C. albicans cells for 24 hours (MOI of 1 for Raws, MOI of 10 for MDMs) and macrophage damage assessed by measuring lactate dehydrogenase release into the supernatant.

FIG. 16A-E shows the results of experiments showing the role of Ece1 in C. albicans mucosal pathogenesis. Infection of cortisone acetate-treated mice with wild-type (BWP17), ece1Δ null mutant or ece1Δ/Δ-ECE1 reverted strain (FIG. 16A) numbers of C. albicans fungi recovered per gram of kidney 3 days post-infection. Fungal invasion, tissue damage and inflammatory cell infiltration of tongue tissue 3 days post-infection by (FIG. 16B) BWP17, (FIG. 16C) ece1Δ/Δ-ECE1 and (FIG. 16D) ece1Δ null mutant, indicating that the ece1Δ null mutant does not invade, damage or recruit inflammatory cells. (FIG. 16E) tongue section 3 days post-infection with BWP17 immunostained with MPO and CD15 markers of neutrophils. **=P<0.01.

Figure 17:
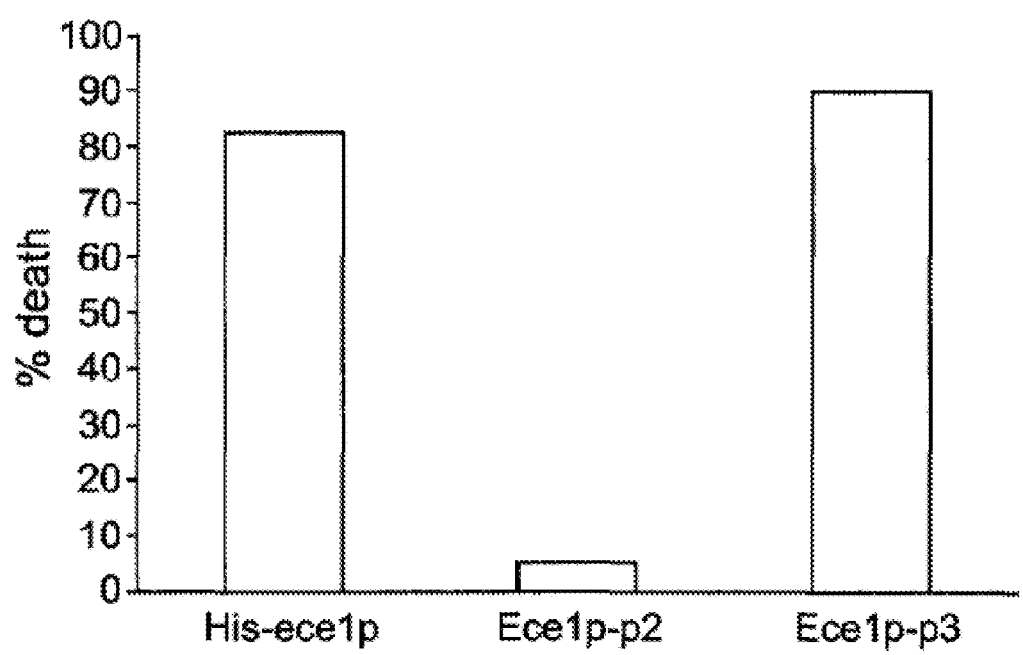

FIG. 17 is a graph showing the results of an experiment to show Drosophila killing by Ece1-III. The percentage of Drosophila death, 24 hours post-infection of 250 µg/ml His-tagged full length Ece1p, Ece1-II (peptide 2) (FIG. 2), and Ece1-III (peptide 3), into a cohort of 20 age-matched flies.

EXAMPLE 1

The Role of Ece1 in Host Cell Damage

To investigate the role of Ece1 in host cell damage, a series of C. albicans gene deletion mutants lacking ECE1, as well as revertant mutant strains were created. Specifically, C. albicans gene deletion cassettes were generated using the PCR-based method described by Dalle F et al. Cellular Microbiology 2010; 12:248-71. Primers ECE1-FG and ECE1-RG as shown below as SEQ ID NO 4 and 5 respectively, were used to amplify the HIS1 and ARG4 markers from plasmids pFA-HIS1 and pFA-ARG4, respectively. The C. albicans strain BWP17 (Wachtler B, et al. Antimicrobial Agents and Chemotherapy 2011; 55:4436-9) was sequentially transformed as described by Wachtler B, et al. PloS one 2011; 6:e17046, with the ECE1-ARG4 and ECE1-HIS1 deletion cassettes and then transformed with the Candida integrating plasmid 10 or CIp10 (Murad et al. Yeast (2000) 16, 4, p325-327), yielding the ece1Δ deletion strain. For generation of the complemented strain, the ECE1 open reading frame, plus upstream and downstream intergenic regions were amplified with primers ECE1-RecF3k (SEQ ID NO 6) and ECE1-RecR (SEQ ID NO 7) and cloned into plasmid CIp10 at MluI and SalI sites, yielding plasmid CIp10-ECE1. This plasmid was transformed into the uridine auxotrophic ece1Δ-deletion strain, yielding the ece1Δ/Δ-ECE1 complemented strain.

```
Primers:
ECE1-FG
                                    (SEQ ID NO 4)
ATCAAATAACCCACCTATTTCAAAATTGTTTTATTTTTGTTTATCTCTAC
AACAAACAACTTTCCTTTATTTTACTACCAACTATTTTCCATTCGTTAAA
gaagcttcgtacgctgcaggtc ECE1-RG
                                    (SEQ ID NO 5)
CACAAAAAACAACAATTAAAAAAATCAGTTACAGCAAAAGTGTCACAAGA
CTTATGGAATAAAAGATTAAGCTTGTGGAAAACAAATTTTTATCTGCTGA
GCATtctgatatcatcgatgaattcgag ECE1-RecF3k
                                    (SEQ ID NO 6)
GCACGCGTCTAAAGTGGAGTAACAAC ECE1-RecR
                                    (SEQ ID NO 7)
GGTCGACCCCAGACGTTGGTTGC
```

Three strains, wild type *C. albicans* (wt), the ECE1 deletion mutant (ece1Δ) and the revertant mutant strain (ece1Δ/Δ-ECE1) were tested. They were applied to three independent human epithelial cell types: oral, gastrointestinal and vaginal. TR146, Caco-2 and A431 epithelial cell lines were maintained as previously described in the Dalle and Wachtler references given above. Epithelial damage assays were performed as previously described by Dalle et al. (supra.) and Wachtler et al. (2011) (supra.) with the following modifications: monolayers in 96 well plates were infected with $2 \times 10^4$ *C. albicans* cells; infections were performed in cell culture media without fetal bovine serum.

After incubation for 24 hours, the damage to the cells was assessed by measuring lactate dehydrogenase (LDH) release using a conventional assay method.

The results are shown in FIG. 1A-C. They show that deletion of ECE1, prevented or reduced *C. albicans* damage in all three cell types. As *C. albicans* is often found associated with the oral, gastrointestinal and urogenitary sites as a member of the natural microbiome, but can also cause infections at such sites, these data suggest that the ECE1 gene product is involved *C. albicans* pathogenicity.

EXAMPLE 2

Role of Peptides

It has been demonstrated that Ece1 can be proteolytically processed by Kex2 into eight peptide fragments (O. Bader et al. BMC Microbiology 2008, 8:115). FIG. 2 illustrates the structure of Ece1 and the proposed resultant peptide fragments following proteolytic processing as well as its phylogenic relationship with orthologues in *C. dubliniensis* and *C. tropicalis* (note that ECE1 orthologues are only found in these two fungal species). Each of the individual *C. albicans* peptides were synthesised by ProteoGenix using fmoc solid phase peptide synthesis technology.

The method of Example 1 was then repeated using a 1:1 mixture of peptides (1-7) of FIG. 2 on human TR146 oral epithelial cells at various concentrations (250 μg/ml, 125 μg/ml, 62.5 μg/ml, 31.25 μg/ml, 15.625 μg/ml and 7.8 μg/ml of each individual peptide within the mixture) or peptide 3 (SEQ ID NO 1) alone in the presence of the ece1Δ mutant *C. albicans*. Peptide 8 could not be included, as this peptide was insoluble. After incubations for 24 hours, the damage was assessed by measuring LDH release as before. The results are shown in FIG. 3A. This shows that peptide 3 (designated Ece1-III in the Figure) produced similar levels of damage to the combination at a concentration of 250 μg/ml.

The test was then repeated using each peptide individually without *C. albicans* cells. The results are shown in FIG. 3B and 3C. They show that whilst peptide 3 was capable of damaging both oral epithelial and vaginal cells, the other peptides displayed essentially no cytolytic activity. Therefore, peptide 3 of processed Ece1 ("Ece1-III" of SEQ ID NO 1) is sufficient to cause lysis of human epithelial cells.

EXAMPLE 3

Cytolytic Activity of Peptides

In order to investigate the cytolytic activities of Ece1-III in greater detail, a haemolysis assay was carried out. Human blood was collected with the SARSTEDT blood collection system and EDTA-coated tubes, washed once with HBSS, resuspended in HBSS and stored at 4° C. for up to one week for experiments. Blood was obtained from healthy human donors.

Each individual peptide (at a final concentration of 30 μg/ml) was incubated with $1 \times 10^7$ human erythrocytes in a volume of 150 μl. After incubation for 1 hour at 37° C., haemolysis was assayed by measuring haemoglobin release, as indicated by absorbance at 541 nm, normalised to a 100% lysis-water control.

The results are shown in FIG. 4. Exposure of human erythrocytes to Ece1-III, but not to the other peptides, resulted in lysis of these cells. It should be noted that, in contrast to epithelial cells, erythrocytes do not contain nuclei and cannot transcriptionally respond to stimuli. Therefore, lysis of erythrocytes by Ece1-III was due to direct cytolysis.

EXAMPLE 4

Pore Formation

Figure 5B:
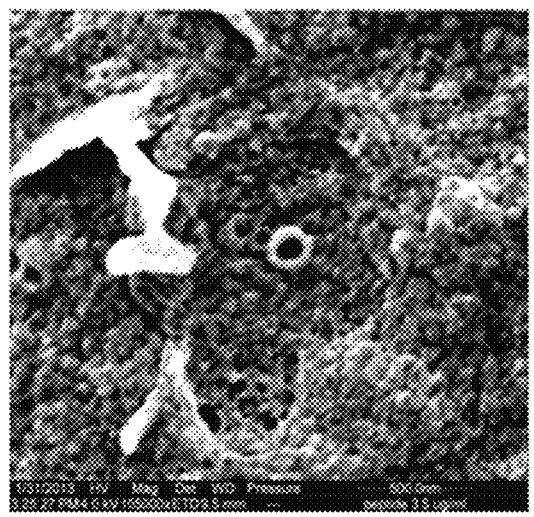

Many peptide toxins elicit cytotoxicity via pore formation and ion influx across membranes. Whether addition of Ece1-III to epithelial cells was able to directly induce pore formation was then tested. Oral epithelial (TR-146) monolayers were incubated with 5 μg/ml Ece1-III of SEQ ID NO 1 for 5 hours and pore formation assessed by scanning electron microscopy. The results are shown in FIG. 5A,B where FIG. 5B shows a further magnified view of the region shown in FIG. 5A. Electron microscopy suggests that Ece1-III can directly induce pores (FIG. 5A,B), which is in agreement with the view that Ece1-III can act as a pore-forming toxin.

EXAMPLE 5

Ion-Dependency of Haemolytic Activity

Since the mode of action of many peptide and pore-forming toxins is ion-dependent, Ece1-III and erythrocytes were co-incubated in the presence of increasing concentrations of the divalent cation chelator, ethylenediaminetetraacetic acid (EDTA), which restricts the bioavailability of divalent cations. After 1 hour, haemolysis was measured as described in Example 3 above. The results, shown in FIG. 6A, indicate that increasing concentrations of EDTA blocked the haemolytic activity of Ece1-III. This effect was reversed by supplementation with magnesium (FIG. 6B). Therefore, like previously described peptide toxins, the haemolytic activity of Ece1-III appears to be ion-dependent.

EXAMPLE 6

Activation of Immune Responses

Pore-forming toxins are generally strong activators of inflammatory responses. Previously it has been shown that recognition of *C. albicans* hyphae resulted in the activation of the mitogen-activated protein kinase (MAPK) p38 signalling pathway and the c-Fos transcription factor, which in turn activates proinflammatory cytokine production (Moyes D L, et al.: *Cell Host Microbe* 2010, 8:225-235,). An extensive screen of >100 *C. albicans* mutants was carried out using protocols described in this reference and also Moyes D L, et al. *PLoS ONE* 2011, 6:e26580; Murciano C. et al. *Infect. Immun* 2011, 79:4902-4911; Moyes D L, et al. *Med Microbiol Immunol* 2012, 201:93-101; Moyes D L, et al. *Methods Mol Biol* 2012, 845:345-360 and Murciano C, et al. *PLoS ONE* 2012, 7:e33362.

The results demonstrated that only a strain deleted in ECE1 was unable to activate the c-Fos pathway (FIG. 7A) or proinflammatory cytokines (FIG. 7B) from oral epithelial cells whilst still producing hyphae. Therefore, activation of epithelial immune responses via c-Fos against *C. albicans* is the result of the action and/or recognition of Ece1.

EXAMPLE 7

Functional Requirements of Ece1-III

Having identified Ece1-III as the region of Ece1 responsible for cellular lysis and the activation of immune responses, the applicants next investigated the precise functional requirements of the Ece1-III amino acid sequence (FIG. 8A). Accordingly, individual peptide fragments corresponding to internal regions of Ece1-III were constructed (WTSA peptides 1-6 (SEQ ID NOS 8-11, 3 and 12 respectively: FIG. 8B). The sequence of each WTSA peptide was chosen to facilitate a detailed examination of each of the internal amyloidogenic regions of Ece1-III, either alone (WTSA peptides 1, 2, 4 and 5), or in combination (WTSA 3). An additional fragment of Ece1-III lacking both amyloidogenic regions was also created (WTSA 6: FIG. 8B). The WTSA peptides were analysed for their ability to cause epithelial cell lysis. However, none of the individual WTSA peptide fragments were observed to induce cell lysis (FIG. 9). Notably, when WTSA 3 and 6 were applied to epithelial cells in combination, (which together constitute the entire Ece1-III peptide sequence) the ability to induce cell lysis was not restored. The WTSA peptides were then analysed for their ability to stimulate secretion of proinflammatory cytokines from oral epithelial cells. None of the WTSA peptides stimulated significant levels of cytokine secretion (FIG. 10A-E). In contrast, a potent induction of all cytokines was observed following exposure to full length Ece1-III. Taken together, these data indicate that only intact, full length Ece1-III is capable of inducing cellular lysis and stimulation of the inflammatory response in epithelial cells.

The p38/c-Fos pathway is activated via the interaction of *C. albicans* hyphae with the surface receptor EGFR (epidermal growth factor receptor), as blocking EGFR activation also blocks c-Fos activation (FIG. 11A). Biacore binding assays show that Ece1-III (of SEQ ID NO 1), but not other parts of the Ece1 protein, directly interact with EGFR with high affinity (FIG. 11B) and that blocking EGFR abolishes the ability of Ece1-III to activate c-Fos (FIG. 11C). Furthermore, blocking EGFR also reduced/abolished activation of all three MAPK signalling pathways (p38, JNK and ERK1/2) (FIG. 12A-C) This demonstrates that activation of mucosal immune responses via the p38/c-Fos pathway is the result of Ece1-III/EGFR interactions and that EGFR plays a primary role in the activation of cell signalling by Ece1-III.

EXAMPLE 8

Interaction of Ece1-III with Phospholipids

In order to insert into a target membrane, a pore-forming peptide toxin must interact with components of the membrane. Because Ece1-III consists of a predicted alpha helix with a dibasic (lysine, arginine) C-terminal head, the applicants predicted that these cationic, positively charged residues may interact with negatively charged phospholipids present in target membranes. Ece1-III was used to probe a phospholipid array (PIP Strip membrane). Binding was assessed by hybridisation with anti-Ece1-III antibody, followed by detection with anti-rabbit antibody conjugated to horse radish peroxidase. The results are shown in FIG. 13. These show that Ece1-III interacts with Phosphatidylinositol-3-phosphate, Phosphatidylinositol-4-phosphate, Phosphatidylinositol-5-phosphate, Phosphatidylinositol-3,4-phosphate, Phosphatidylinositol-3,5-phosphate, Phosphatidylinositol-4,5-phosphate, Phosphatidylinositol-3,4,5-phosphate, Phosphatidic acid and Phosphatidylserine, with binding to Phosphatidylinositol-3-phosphate being particularly robust (FIG. 13). Ece1-III did not interact with Lysophosphatidic acid, Lysophosphatidylcholine, Phosphatidylinositol, Phosphatidylethanolamine, Phosphatidylcholine or Sphingosine-1-phosphate. Therefore, insertion of Ece1-III into target membranes (pore formation) may be mediated by interactions with phospholipids.

EXAMPLE 9

Ece1 Facilitates Immune Cell Killing

Given the importance of Ece1-III in killing epithelial cells, the applicants examined whether it also plays a role in immune escape of *C. albicans* from macrophages. In vitro, *C. albicans* yeast cells are phagocytosed by macrophages, but rapidly germinate and escape the macrophage via hypha formation. To examine whether Ece1 is involved in this process, wild type, ece1Δ, and ece1Δ/Δ-ECE1 cells were coincubated with macrophages and the following parameters measured: phagocytosis rates, length of hyphae, escape from macrophages, and damage of macrophages. Interestingly, ece1Δ cells were phagocytosed by macrophages at the same rate, formed hyphae within macrophages of the same length, and even escaped from macrophages at the same rates as the wild type, but were unable to damage these immune cells (FIGS. 14A-C and 15). These data demonstrate that *C. albicans* hyphae can non-lytically escape from macrophages, and indicate a specific role for Ece1 in host cell damage.

EXAMPLE 10

Effect of Ece1 on Mucosal Pathogenciity in Vivo

Figure 16A:
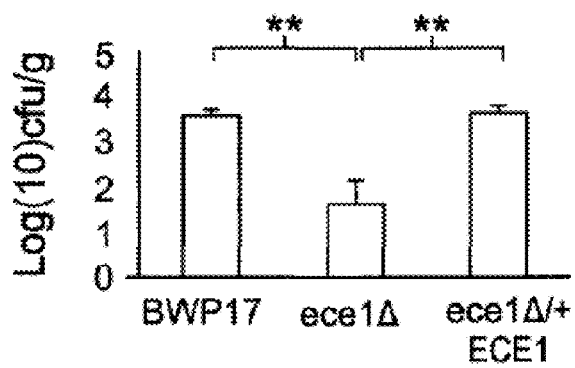
Figure 16B:
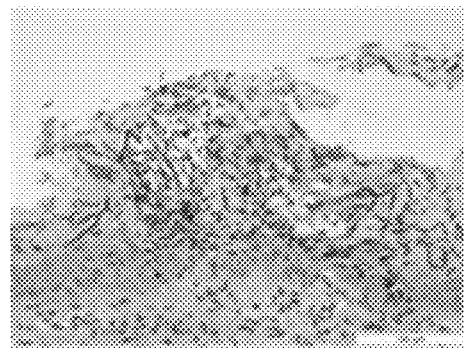
Figure 16C:
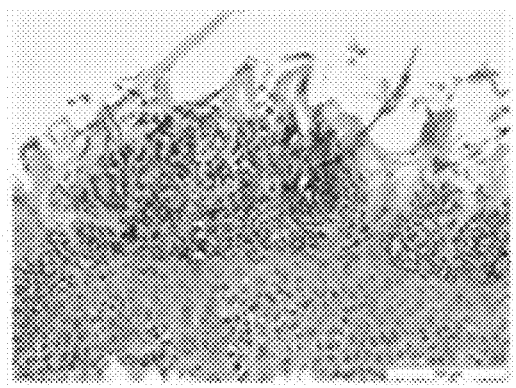
Figure 16E:
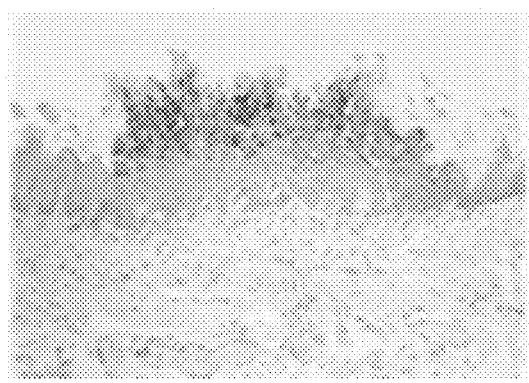
Figure 16D:
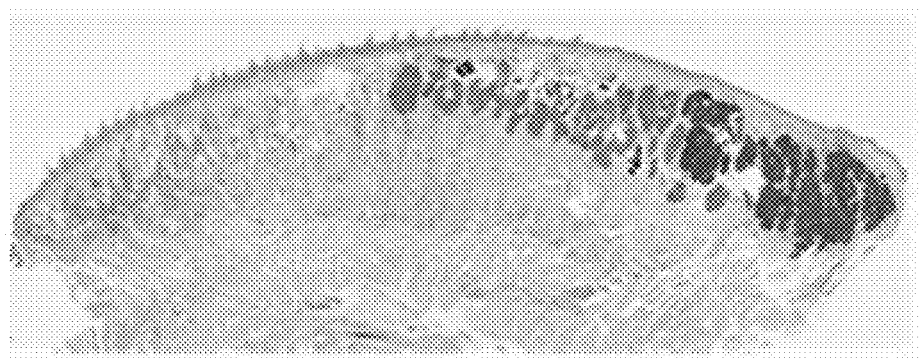

The applicants also tested whether Ece1 was required for mucosal pathogenciity in vivo. To test this, they utilised a murine model of oropharyngeal candidiasis. In this model, mice were first immunosuppressed with cortisone acetate prior to administration of wild-type (parental) *C. albicans* (BWP17), a ece1Δ null mutant and ece1Δ/Δ-ECE1 revertant strain into the oral cavity. After four days, fungal burdens, fungal invasion, tissue damage and immune cell recruitment was determined in tongue tissues. Significantly lower fungal burdens were found in mice infected with the ece1Δ null mutant as compared with the wild-type (BWP17) or the ece1Δ/Δ-ECE1 revertant strains, and in many cases the ece1Δ null mutant could not be recovered from mice (FIG. 16A). Histological analysis of mouse tongues in both the wild-type (BWP17) and ece1Δ/Δ-ECE1 revertant strain showed multiple foci of infection that were associated with inflammatory immune cells (neutrophils) and extensive local tissue damage (FIG. 16B-D). In contrast, mice infected with the ece1Δ null mutant showed no evidence of any foci of invasion, tissue damage or inflammation and no evidence of *C. albicans* was detectable (FIG. 16E). Therefore, Ece1 is essential for successful mucosal infection, damage induction and immune activation in this model.

EXAMPLE 11

Effect of Ece1 and Ece1-III on *Drosophila melanogaster*

The applicants also determined the effect of administering full length His-tagged Ece1p and Ece1-III in a *Drosophila melanogaster* (fruit fly) model. All flies injected with full length His-tagged Ece1p and Ece1-III displayed signs of paralysis, with only 17.5% and 10% recovering after 24 hours, as compared with the negative control Ece1-II (peptide 2) which showed no signs of paralysis (FIG. 17). This indicates that Ece1-III may have a direct or indirect neurotoxic effect.

CONCLUSION

These data provide evidence that Ece1 (and its active component Ece1-III) has a dual functional role, by acting both as a pore-forming toxin that damages host cells and as an activator of immune responses. Damage of host cells and uncontrolled immune activation are the hallmarks of several diseases caused by *C. albicans*, which can often lead to death (45-76% mortality) during systemic infections. Therefore, neutralisation of Ece1-III will prevent not only host damage during *C. albicans* infections but also deleterious inflammatory responses. This indicates that Ece1-III represents a new therapeutic target to treat *C. albicans* infections.

---

The invention claimed is:

1. A pharmaceutical composition comprising a peptide and a pharmaceutically acceptable carrier, wherein the peptide consists of SEQ ID NO:1, SEQ ID NO:16, or SEQ ID NO:17,

```
                                        (SEQ ID NO: 1)
        SIIGIIMGILGNIPQVIQIIMSIVKAFKGNKR (SEQ ID NO: 16)
        SIIGILTAILNNVPQIINVITTIIKSIITGNKR (SEQ ID NO: 17)
        ISFAGIVSSIINQLPSIIQIIGNIIKAGLVKR.
```

2. The pharmaceutical composition of claim 1, wherein the peptide consists of SEQ ID NO:1.

3. The pharmaceutical composition of claim 1, wherein the peptide consists of SEQ ID NO:16.

4. The pharmaceutical composition of claim 1, wherein the peptide consists of SEQ ID NO:17.

5. A method for prophylaxis or treatment of an infection by *Candida* species, said method comprising administering to a subject in need thereof a non-toxic amount of the composition of claim 1, wherein the non-toxic amount is sufficient to produce an immune response that is protective against *Candida* infection.

6. The method of claim 5 wherein the infection is an oral or mucosal infection by *Candida*.

7. The method of claim 6 wherein the infection is a vaginal infection.

* * * * *